(12) United States Patent  (10) Patent No.: US 9,222,862 B2
Karamanos  (45) Date of Patent: Dec. 29, 2015

(54) PIPING STICK SYSTEMS AND METHODS

(71) Applicant: John C. Karamanos, San Jose, CA (US)

(72) Inventor: John C. Karamanos, San Jose, CA (US)

(73) Assignee: John C. Karamanos, San Jose, CA (US)

( * ) Notice: Subject to any disclaimer, the term of this patent is extended or adjusted under 35 U.S.C. 154(b) by 263 days.

(21) Appl. No.: 13/797,941

(22) Filed: Mar. 12, 2013

(65) Prior Publication Data

US 2014/0261725 A1  Sep. 18, 2014

(51) Int. Cl.
*F24F 7/00* (2006.01)
*G01N 3/12* (2006.01)
*G01M 3/26* (2006.01)

(52) U.S. Cl.
CPC .. *G01N 3/12* (2013.01); *F24F 7/00* (2013.01); *G01M 3/26* (2013.01); *Y10T 137/0402* (2015.04); *Y10T 137/8158* (2015.04)

(58) Field of Classification Search
CPC ........ G01N 3/12; G01M 3/26; G01M 3/2815; Y10T 137/8158; Y10T 137/0402; F24F 7/00
USPC ............................................. 137/15.01, 551
See application file for complete search history.

(56) References Cited

U.S. PATENT DOCUMENTS

| 1,429,776 | A | 9/1922 | Robinson |
|---|---|---|---|
| 1,793,059 | A | 2/1931 | Chambers |
| 2,233,273 | A | 2/1941 | Di Vincenzo |
| 2,268,360 | A | 12/1941 | Walker |
| 2,534,690 | A | 12/1950 | Young, Jr. et al. |
| 2,999,605 | A | 9/1961 | De Jarnett |
| 3,182,717 | A | 5/1965 | Pierce |
| 3,216,025 | A | 11/1965 | Roll |
| 3,463,223 | A | 8/1969 | Marino |
| 3,706,125 | A | 12/1972 | Hopkins |
| 3,734,171 | A | 5/1973 | Ares et al. |
| 3,778,537 | A | 12/1973 | Miller |
| 4,099,630 | A | 7/1978 | Beck |
| 4,123,012 | A | 10/1978 | Hough |
| 4,140,227 | A | 2/1979 | Beck |
| 4,163,372 | A | 8/1979 | Frye et al. |
| 4,193,563 | A | 3/1980 | Vitale |

(Continued)

FOREIGN PATENT DOCUMENTS

| JP | 62-008033 | 1/1987 |
|---|---|---|
| JP | 02-035326 | 2/1990 |

(Continued)

OTHER PUBLICATIONS

International Search Report mailed Aug. 13, 2008 for International Application No. PCT/US2006/017797, 13 pages.

(Continued)

*Primary Examiner* — Kevin Lee
(74) *Attorney, Agent, or Firm* — Amin, Turocy & Watson, LLP

(57) ABSTRACT

Embodiments of a piping stick and methods of manufacturing and using a piping stick are disclosed herein. The piping stick can define a scalable volume including a plurality of piping sections and a plurality of control sections. The non-connected in his of the piping sections of the piping stick can be capped. The piping stick can be assembled by assembling the plurality of control sections and the plurality of piping sections, pressurizing, the piping stick at a first time, and determining the integrity of the piping stick by evaluating the pressure in the piping stick at a second time.

14 Claims, 14 Drawing Sheets

(56) References Cited

U.S. PATENT DOCUMENTS

| | | |
|---|---|---|
| 4,244,542 A | 1/1981 | Mathews |
| 4,261,529 A | 4/1981 | Sandberg et al. |
| 4,473,107 A | 9/1984 | Fairbrother et al. |
| 4,541,602 A | 9/1985 | Potzas |
| 4,550,891 A | 11/1985 | Schaty |
| 4,682,647 A | 7/1987 | Sleep |
| 4,779,815 A | 10/1988 | Moore et al. |
| 4,842,227 A | 6/1989 | Harrington et al. |
| 4,971,139 A | 11/1990 | Khattar |
| 5,016,843 A | 5/1991 | Ward |
| 5,050,824 A | 9/1991 | Hubbard |
| 5,278,740 A | 1/1994 | Agnelli |
| 5,417,243 A | 5/1995 | Ragona |
| 5,446,677 A | 8/1995 | Jensen et al. |
| 5,458,241 A | 10/1995 | Brown |
| 5,526,931 A | 6/1996 | White |
| 5,551,630 A | 9/1996 | Enoki et al. |
| 5,597,354 A | 1/1997 | Janu et al. |
| 5,771,954 A | 6/1998 | Benner et al. |
| 5,850,037 A | 12/1998 | Mullins |
| 5,860,627 A | 1/1999 | Edwards |
| 5,986,562 A | 11/1999 | Nikolich |
| 6,079,626 A | 6/2000 | Hartman |
| 6,135,381 A | 10/2000 | Teson |
| 6,142,405 A | 11/2000 | Black |
| 6,170,784 B1 | 1/2001 | MacDonald et al. |
| 6,375,017 B1 | 4/2002 | Schattner et al. |
| 6,385,510 B1 | 5/2002 | Hoog et al. |
| 6,409,223 B1 | 6/2002 | Bartholoma |
| 6,536,516 B2 | 3/2003 | Davies et al. |
| 6,578,319 B1 | 6/2003 | Cole et al. |
| D490,690 S | 6/2004 | Brass et al. |
| 6,868,293 B1 | 3/2005 | Schurr et al. |
| 6,951,324 B2 | 10/2005 | Karamanos |
| 7,062,830 B2 * | 6/2006 | Alles .......................... 29/401.1 |
| 7,092,794 B1 | 8/2006 | Hill et al. |
| 7,140,236 B2 | 11/2006 | Karamanos |
| 7,165,797 B2 | 1/2007 | Karamanos |
| 7,243,004 B2 | 7/2007 | Shah et al. |
| 7,274,973 B2 | 9/2007 | Nichols et al. |
| 7,343,226 B2 | 3/2008 | Ehlers et al. |
| 7,387,013 B2 | 6/2008 | Karamanos |
| 7,444,731 B2 | 11/2008 | Karamanos |
| 7,478,761 B2 | 1/2009 | Karamanos et al. |
| 7,537,183 B2 | 5/2009 | Karamanos |
| 7,856,865 B2 | 12/2010 | Karamanos |
| 7,937,820 B2 | 5/2011 | Karamanos |
| 8,714,236 B2 * | 5/2014 | Karamanos .................. 165/11.1 |
| 2002/0080032 A1 | 6/2002 | Smith et al. |
| 2002/0088273 A1 | 7/2002 | Harness et al. |
| 2003/0050871 A1 | 3/2003 | Broughton |
| 2003/0085022 A1 | 5/2003 | Viso |
| 2003/0085023 A1 | 5/2003 | Viso |
| 2003/0171092 A1 | 9/2003 | Karamanos |
| 2003/0222185 A1 | 12/2003 | Rubenstein et al. |
| 2004/0159110 A1 | 8/2004 | Janssen |
| 2004/0253918 A1 | 12/2004 | Ezell et al. |
| 2005/0039470 A1 | 2/2005 | Laing et al. |
| 2005/0056752 A1 | 3/2005 | Karamanos |
| 2005/0056753 A1 | 3/2005 | Karamanos |
| 2006/0249589 A1 | 11/2006 | Karamanos |
| 2006/0287774 A1 | 12/2006 | Yoon et al. |
| 2007/0262162 A1 | 11/2007 | Karamanos |
| 2008/0195254 A1 | 8/2008 | Jung et al. |
| 2009/0012650 A1 | 1/2009 | Wang et al. |
| 2009/0057499 A1 | 3/2009 | Karamanos |
| 2009/0062964 A1 | 3/2009 | Sullivan et al. |
| 2010/0252641 A1 | 10/2010 | Karamanos |
| 2010/0307733 A1 | 12/2010 | Karamanos et al. |
| 2011/0155354 A1 | 6/2011 | Karamanos et al. |
| 2012/0168113 A1 | 7/2012 | Karamanos |

FOREIGN PATENT DOCUMENTS

| | | |
|---|---|---|
| JP | 05042818 A | 2/1993 |
| JP | 07055195 A | 3/1995 |
| JP | 08189717 A | 7/1996 |
| JP | 2000046375 A | 2/2000 |
| JP | 2001004199 A | 1/2001 |

OTHER PUBLICATIONS

International Search Report mailed Jun. 27, 2008 for International Application No. PCT/US2008/050788, 9 pages.

* cited by examiner

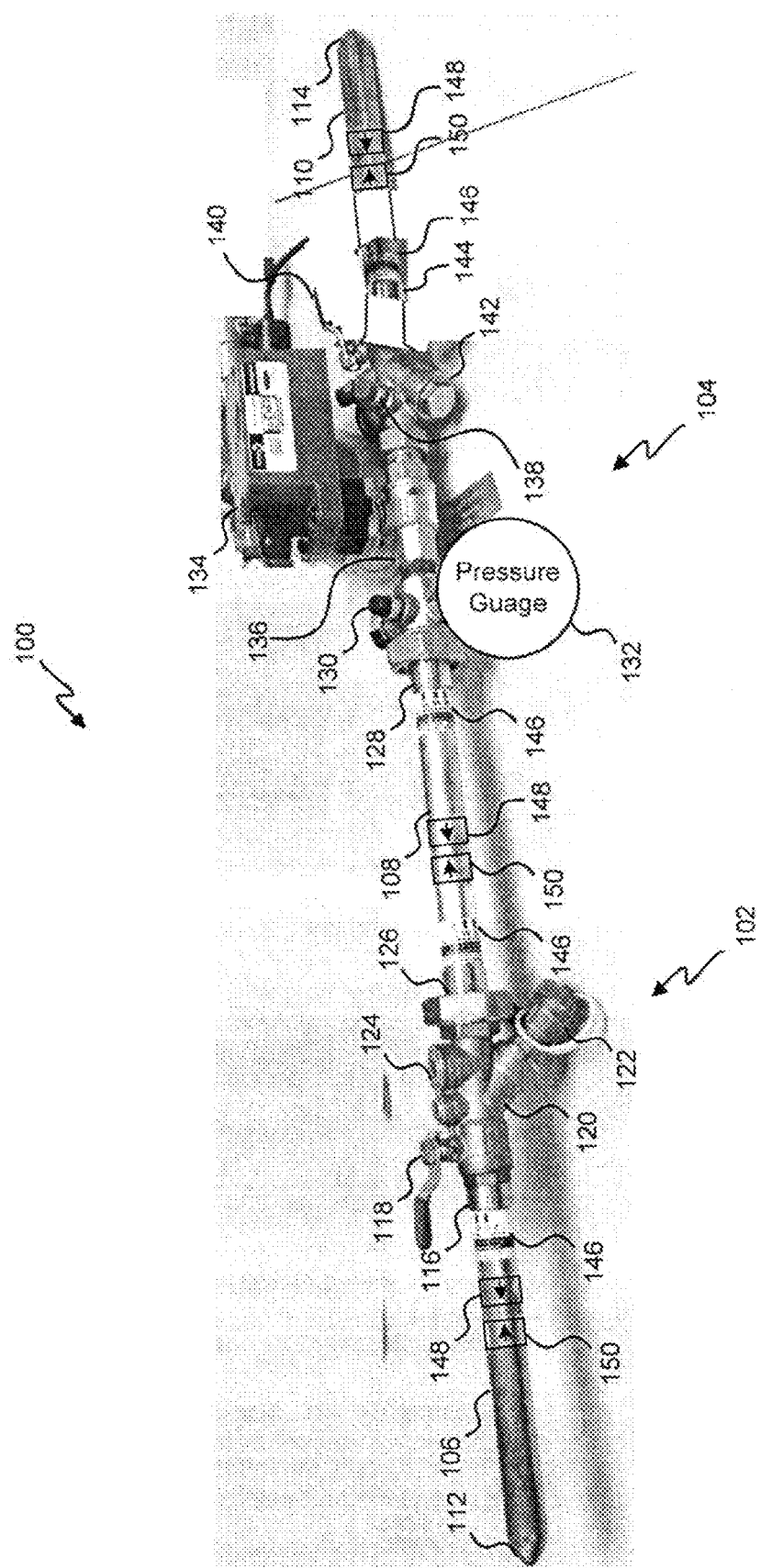

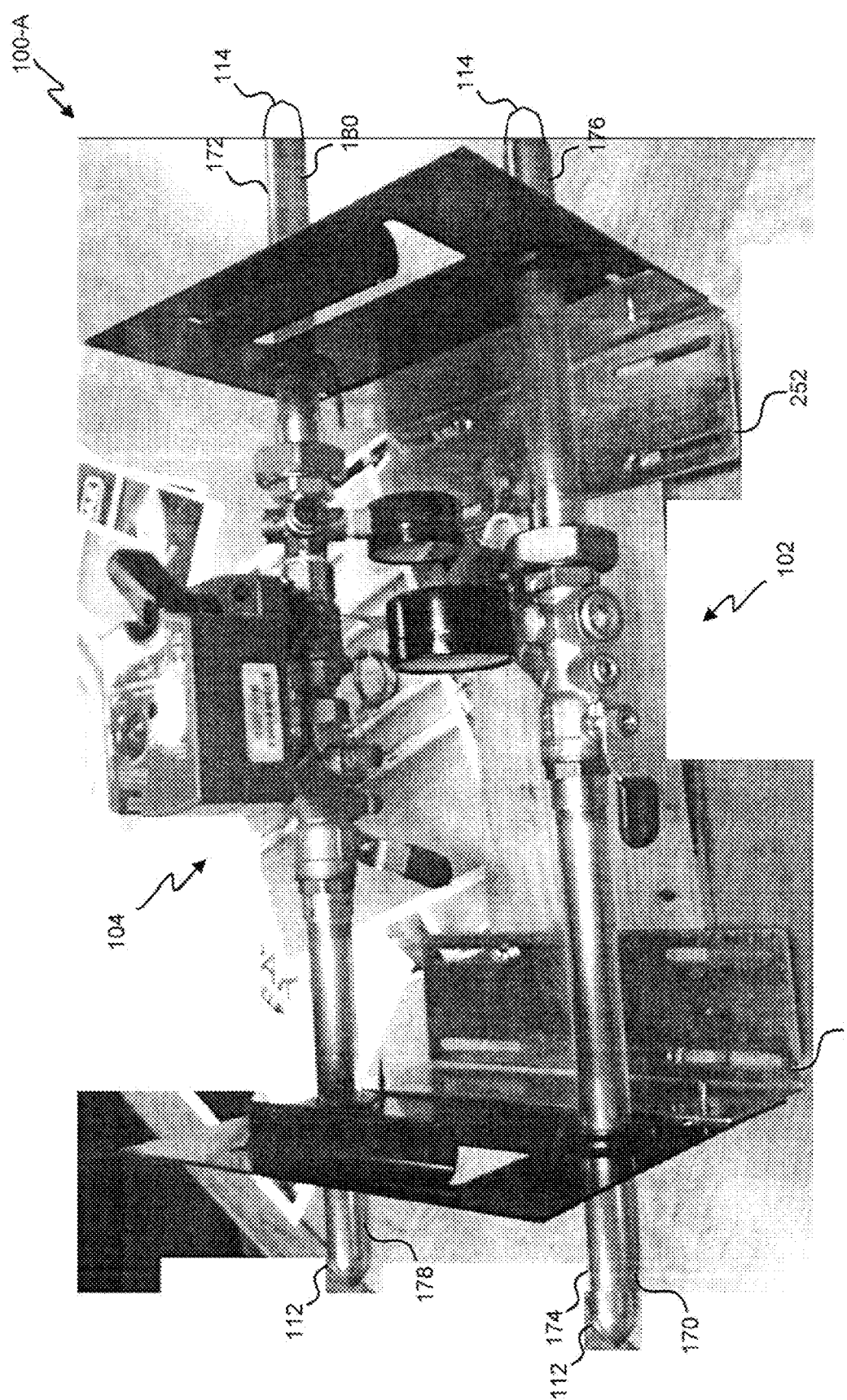

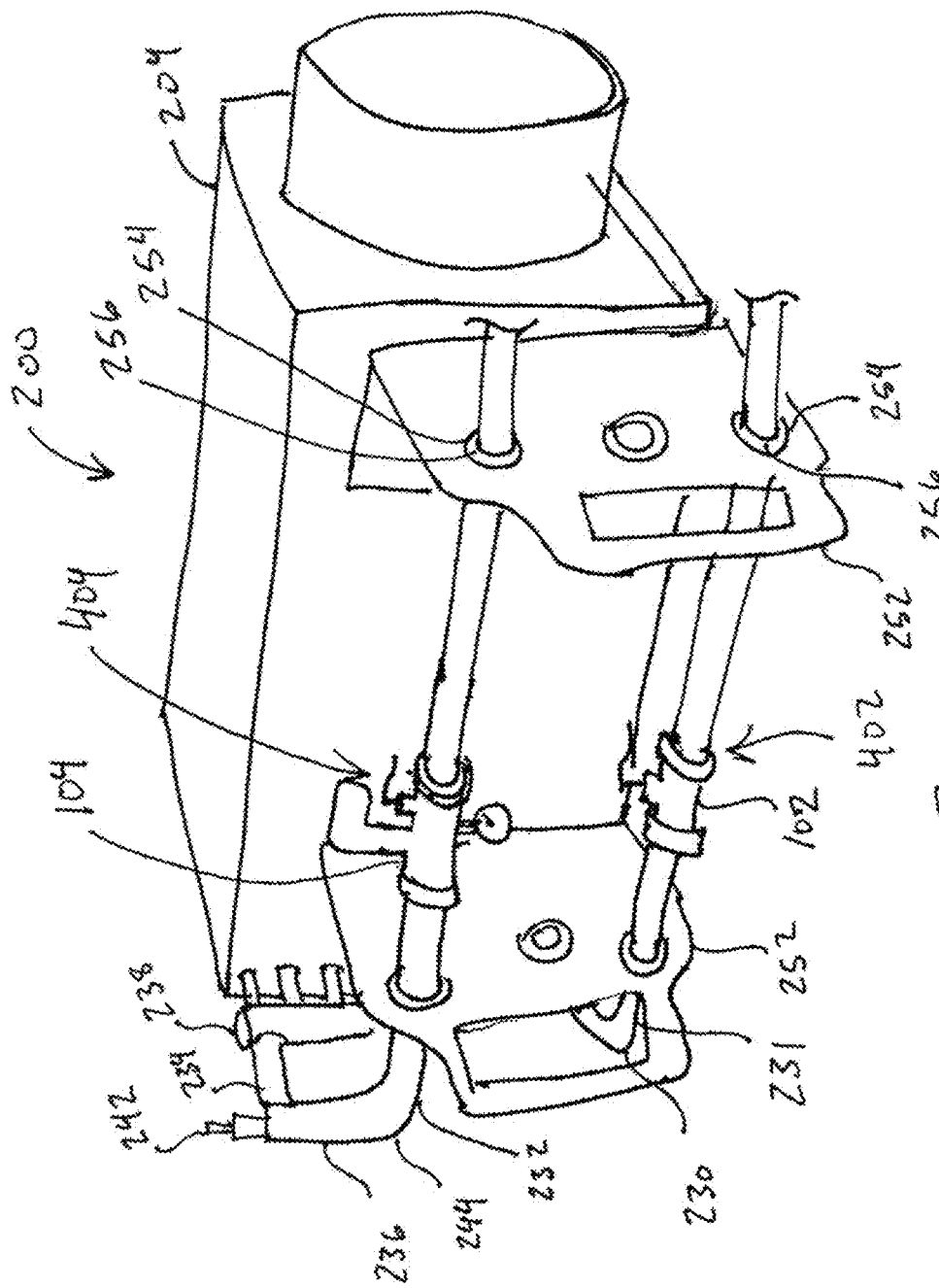

PIPING STICK SYSTEMS AND METHODS

BACKGROUND OF THE INVENTION

Embodiments of the present invention relate to integrated heating, ventilation, and air conditioning (HVAC) systems and methods, and in particular to approaches that include embedded coils and other heat exchangers.

In general, HVAC systems control the temperature and humidity of indoor air. In most HVAC systems, air is drawn in, filtered, cooled and dehumidified or heated and humidified, and then delivered to an air conditioned space. The greatest portion of incoming air is drawn from the air conditioned space for recirculation through the HVAC system. HVAC system includes fans and ductwork for moving conditioned air to where it is needed while passing it through cooling and/or a heating sections of the ductwork.

HVAC systems in residential, commercial, education and research buildings usually include metallic pipes, hollow composite materials such as tubes, and the like. The systems are typically supported from and between floor or ceiling joists. The HVAC system typically includes a primary or main duct. A series of smaller branch ducts which extend from the main duct are mounted between adjacent floor or ceiling joists. Such main and branch ducts are normally supported by metal hangers located between the joists. Often the branch ducts include pipes and conduit lines for transporting liquid or gas which are suspended from ceiling joists or an adjacent wall typically with Unistrut®, threaded rod, couplings, and various hanger brackets.

Piping and conduits that supply gas and/or liquids within buildings benefit from careful preparation. Builders or contractors typically use ladders or scaffolding to reach areas where piping is routed so installation may be cumbersome. Occasionally the pipe or conduits are prepared on the ground and installed by ladder as more complete assemblies. Pipe and conduit assemblies prepared on the ground or a floor of a building under construction are more unwieldy than the unassembled components, but pre-assembly is often more practical. Furthermore, conditions existing at construction sites and the number of differing types of components used in assembling a HVAC system render cataloging known HVAC components a challenge.

Generically, a terminal unit, also sometimes referred to as an air handling unit, is a HVAC system component that is located near an air conditioned space that regulates the temperature and/or volume of air supplied to the space. When providing air to a more critical environment such as a laboratory, an almost identical ductwork section is frequently referred to as a lab valve damper rather than as a terminal unit, with the distinction generally relating to the precision with which the unit controls the temperature and humidity of conditioned air. As used throughout this document, the phrase terminal unit encompasses either a terminal unit or a lab valve damper.

A HVAC system may be assembled using any one of several different types of terminal units. Generally, the mechanical portion of a terminal unit includes a casing through which air flows during operation of a HVAC system. Accordingly, the casing includes an inlet for receiving air from ductwork of a HVAC system, and an outlet for supplying air to a space in a building. Casings are usually fabricated from 22 gauge galvanized sheet steel. Due to the use of such light material, casings are easily damaged during shipping to a building site and during installation into the HVAC system. Those familiar with such damage to terminal unit casings frequently refer to it as "oil canning" because it resembles how a light gauge oil can collapses as the liquid flows out.

In a typical hydronic (all-water) HVAC system, the mechanical portion of a terminal unit includes a heat exchanging coil. Heated, and/or cooled water is pumped from a central plant through pipes to the coil. Air from the HVAC system's ductwork passes through the coil after entering and before leaving the casing. Usually, a single terminal unit is dedicated for heating and/or cooling each air conditioned space. Air from the duct connected to the terminal unit passes through the coil to be heated and/or cooled by water flowing through the coil before the air enters the air conditioned space.

A Variable Air Volume ("VAV") HVAC system, in response to a control signal from a thermostat or room sensor, supplies only that volume of hot and/or cold air to an air conditioned space needed to satisfy the space's thermal load. A VAV HVAC system meets-changing cooling and/or heating requirements by adjusting the amount, rather than the temperature, of air that flows to a space. For most buildings, a VAV HVAC system yields the best combination of comfort, first cost, and life cycle cost.

A VAV terminal unit is a relatively complex assembly which includes sheet metal, plumbing, electrical and pneumatic components. For example, a VAV terminal unit includes an airflow sensor that senses the velocity of air entering the terminal unit. To adjust the volume of cold air, a VAV terminal unit frequently includes a damper which automatically opens and closes as needed.

As a thermal load of a space decreases, the damper starts closing thereby reducing the amount of heated or cooled air supplied to the space. Alternatively, the volume of air entering a space may be controlled by varying the speed of a fan included in the terminal unit. For either type of VAV terminal unit, VAV HVAC systems save energy consumed by fans in comparison with alternative HVAC systems by continually adjusting airflow to the heating and/or cooling required.

To be operable and fully-functional, terminal units for a hydronic HVAC system often include a coil, ductwork for supplying air to the coil and receiving air from the coil, plumbing for supplying water into and receiving water from the coil, and a control valve for regulating the amount of water flowing through the coil.

To match the flow of air through the terminal unit's ductwork to the profile of the coil, the terminal unit's ductwork may include transition sections both for air entering the coil and for air leaving the coil. In addition, a terminal unit may also include a re-heat coil, and/or a sound attenuator. In a terminal unit adapted for use in a VAV HVAC system, the terminal unit's ductwork may also include a damper and a damper actuator or variable speed fan for controlling the volume of air supplied by the terminal unit, and an airflow sensor for sensing the volume of air passing through the terminal unit.

Usually, all of the various parts needed to assemble a fully-functional VAV HVAC system's terminal unit arrive at building construction sites as separate components. Generally, these components are then assembled into a fully functional terminal unit at the construction site. Due to cluttered working conditions usually existing at a construction site where workers skilled in different crafts, e.g. plumbing, electrical, structural, etc., must concurrently collaborate to complete the building project, assembling the various components into a fully functional terminal unit may occupy the better part of a day. Furthermore, present practices and equipment are poorly adapted for swiftly constructing a high quality HVAC system that is easily commissioned.

For example, because it is less expensive to wire a HVAC system's terminal units with 24 volt low voltage electrical power rather than 220 or 110 volt power, presently sections of buildings include transformer trees which an electrician generally assembles by installing multiple step down transformers on an electrical panel. This technique permits wiring 220 or 110 volt electrical power to the transformer tree on each panel, with the 24 volt low voltage electrical power then being wired individually from a transformer on the panel over distances of five (5) to one, hundred (100) feel to a terminal units for energizing its Direct Digital Control ("DDC") controller, and 2 way or 3 way automatic temperature control ("ATC") control valve.

Usually, terminal units are supported from a building using angle brackets, straps, or thread rod. Usually these support devices are attached directly to the terminal unit. Terminal unit casings are usually made using 22 gauge sheet metal. Due to the use of this light material, casings are easily dented or bent during installation.

With current construction site labor costing up to $80.00/hour or more, assembling a terminal unit at a construction site may cost $500.00 to $1,000.00 for labor alone. Furthermore, terminal units assembled at a construction site generally differ from one another due to assembly by different craftsmen, and insufficient use of identical components in assembling each terminal unit. Due to conditions existing at construction sites and the number of differing types of components used in assembling a HVAC system, cataloging the components used in assembling the system is impractical. Lastly, construction sites generally lack any facilities for individually pre-testing building components, such as terminal units, assembled on-site.

After assembling a HVAC system, it should be activated, tested and commissioned to ensure IAQ. Testing a HVAC system only after it is completely assembled inevitably results in many hours of problem-solving and leak-hunting. Usually, mere are leaky joints, broken valves, damaged pipes, leaky coils and improperly assembled components that must be tracked down which further increases building costs. After finding a faulty component, it must be identified, ordered and replaced which takes time and delays completion of the building project. Furthermore, years after a building project is complete to maintain IAQ a building manager responsible for the HVAC system's maintenance will often have to identify and replace broken components.

The preceding considerations arising from construction site assembly of fully functional terminal units slows construction, increase building costs, requires rework when a terminal unit experiences an initial failure, and ultimately makes more difficult and expensive maintaining a building's HVAC system years after those responsible for its assembly are no longer available.

Current techniques for implementing HVAC systems often required ancillary components such as flow controls, ATC valves, and the like to be added to HVAC piping structures in the field or at a jobsite construction location. Relatedly, such ancillary components, piping structures, and the like may be susceptible to damage during transport. What is needed are improved HVAC systems and methods that allow HVAC components to be configured prior to shipping, and to be shipped without risk of damage. Embodiments of the present invention provide solutions for at least some of these needs.

BRIEF SUMMARY OF THE INVENTION

In one embodiment, the present disclosure provides a method of manufacturing an HVAC system. The method includes obtaining a piping stick that has a first tubular end section, a second tubular end section, a sealed and pressurized interior lumen defined at least in part by the first and second tubular end sections, a pressure gauge in fluid communication with the interior lumen and indicating a non-atmospheric pressure therein, a first valve coupled with the first end section, and a second valve coupled with the second end section, reading the pressure gauge to verify that the sealed interior lumen of the piping stick is pressurized to the non-atmospheric pressure, cutting the piping stick to create a first portion including the first valve and the first tubular end section and a second portion including the second valve and the second tubular end section, and incorporating the first and second portions into the HVAC system.

In some embodiments of the method of manufacturing an HVAC system, the first tubular end section can include a sealed end and a non-sealed end connecting to the first valve. In some embodiments of the method of manufacturing an HVAC system, the method can include cutting the first tubular end section between the sealed end and the non-sealed end so as to separate the sealed end from the first valve. In some embodiments of the method of manufacturing an HVAC system, the second tubular end section can include a sealed end and a non-sealed end connecting to the first valve. In some embodiments, the method can include cutting the second tubular end section between the sealed end and the non-sealed end so as to separate the sealed end from the second valve.

In some embodiments of the method of manufacturing an HVAC system, the piping stick can include an indicator of the location for cutting the piping stick to create a first portion and a second portion, and in some embodiments of the method of manufacturing an HVAC system, cutting the piping stick to create a first portion and a second portion can include cutting the piping stick at the indicated location.

In some embodiments of the method of manufacturing an HVAC system, the non-atmospheric pressure can be a super-atmospheric pressure, and in some embodiments of the method, of manufacturing an HVAC system, the non-atmospheric pressure can be a subatmospheric pressure. In some embodiments of the method of manufacturing an HVAC system, the first valve and the second valve are open.

In some embodiments the method of manufacturing an HVAC system includes reading the pressure gauge to verify the sealed interior lumen of the piping stick is pressurized to the non-atmospheric pressure can verify that the first tubular end section and the second tubular end section are pressurized to she non-atmospheric pressure.

In some embodiments of the method of manufacturing an HVAC system, the first control section comprises a single flow assembly that can be, for example, an inlet piping section assembly, and the second control section comprises a single flow assembly that can be, for example, an outlet piping section. In some embodiments of the method of manufacturing an HVAC system, the first control section can comprise a plurality of flow assemblies which can be, for example, a plurality of inlet piping sections, a plurality of outlet piping sections, or a plurality of both inlet and outlet piping sections. In some embodiments of the method of manufacturing an HVAC system, the second control section can comprise a plurality of flow assemblies which can be, for example, a plurality of inlet piping sections, a plurality of outlet piping sections, or a plurality of both inlet and outlet piping sections. In some embodiments in which one or both of the first and/or second control sections comprises a plurality of flow assemblies, the flow assemblies in the plurality of flow assemblies can be connected to each other by piping sections.

In one embodiment, the present disclosure provides a method of manufacturing a piping stick. The method includes, connecting a first hydronic unit to a first tubular end section and a tubular interior section, connecting a second hydronic unit to a second tubular end section and the tubular interior section, the second hydronic unit including a pressure gauge, sealing a first end of the first tubular end section and a first end of the second tubular end section, pressurizing the tubular interior section to a non-atmospheric pressure, and validating the pressure of the tubular interior section.

In some embodiments, the method of manufacturing a piping stick includes adding an indicator of a location along the tubular interior section. In some embodiments of the method of manufacturing a piping stick, the indicator of the location along the tubular interior section comprises an adhered indicator. In some embodiments, the method of manufacturing a piping stick includes adding an indicator of a location along the first tubular end section, and in some embodiments, the method of manufacturing a piping stick includes adding an indicator of a location along the second tubular end section. In some embodiments, the method of manufacturing a piping stick includes validating the pressure in the first tubular end section and the second tubular end section.

In one embodiment, the present disclosure provides a piping stick. The piping stick includes a first pipe having a first sealed end and a second open end, a first control section attached to the second open end of the first pipe, a second pipe including a first open end attached to the first control section and a second open end, a second control section attached to the second open end of the second pipe, and a third pipe having a first open end attached to the second control section and a second sealed end. In some embodiments, the piping stick is pressurized to a non-atmospheric pressure.

In some embodiments of the piping stick, the control section includes a pressure gauge, and in some embodiments, the piping stick includes an indicator located along one of the first pipe, the second pipe, and the third pipe, and indicating the location for the placement of a cut. In some embodiments, the piping stick can include a first flow direction indicator associated with the first control section and a second flow direction indicator associated with the second control section, and in some embodiments, the first flow direction indicator can be distinguishable from the second flow direction indicator.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIG. 1 is a perspective view of a piping stick according to one embodiment of the present invention.

FIG. 1A is a perspective view of a two piece piping stick according to one embodiment of the present invention.

FIG. 4A is a perspective view of a fully-functional zone-control unit ready for installation in a HVAC system, the zone-control unit includes a casing from which a pair of handles project, and control sections connected to inlet and outlet assemblies.

Figure 2:
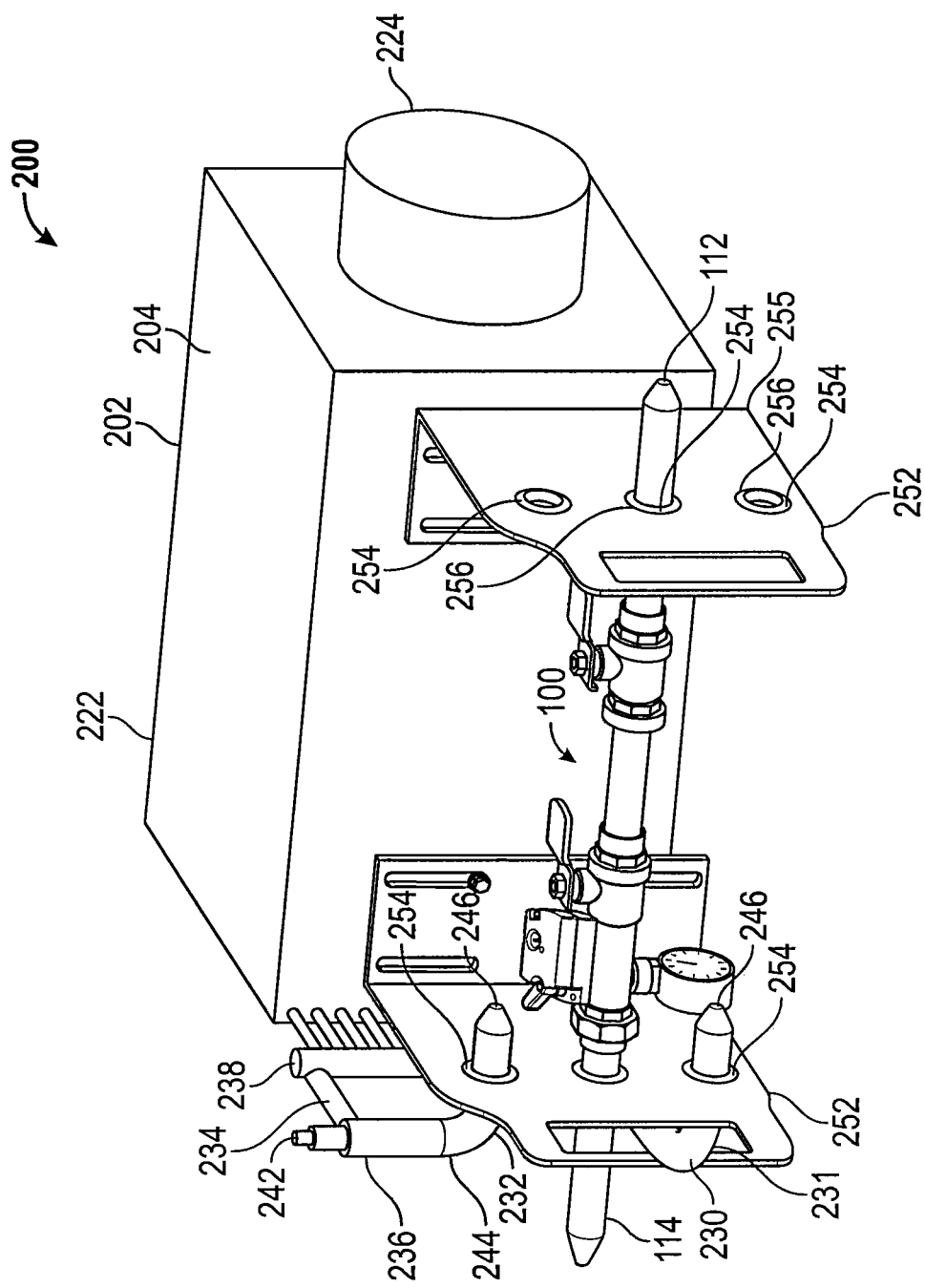
FIG. 2 is a perspective view of a fully-functional zone-control unit ready for installation in a HVAC system, the zone-control unit includes a casing from which a pair of handles project that can receive and/or retain the piping stick, according to one embodiment of the present invention.

In the appended figures, similar components and/or features may have the same reference label. Where the reference label is used in the specification, the description is applicable to any one of the similar components having the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

The ensuing description provides preferred exemplary embodiment(s) only, and is not intended to limit the scope, applicability or configuration of the disclosure. Rather, the ensuing description of the preferred exemplary embodiments) will provide those skilled in the art with an enabling description for implementing a preferred exemplary embodiment. It is understood that various changes may be made in the function and arrangement of elements without departing from the spirit and scope as set forth in the appended claims.

Attached are pictures of various bracketing devices in addition to handles that can be used with the piping stick, also referred to as the Koil Pak. The piping stick can ship in one piece with, or without brackets installed tor mounting on to sheetmetal duct/casing, or as an individual set with brackets.

In describing the background, focus is on terminal units with hot water re-heat. A person of skill in the art will recognize that the piping stick can be used with any fluid coil/thermal transfer device including thermal transfer devices configured to heating, cooling, and/or for steam. In some embodiments, the fluid coil/thermal transfer device can include and/or be associated with, for example, fan coils, one or several air handling units (AHU), one or several chilled beams, one or several water source heat pumps, one or several radiant panels, one or several fin tubes, one or several convectors, etc.

The perspective view of FIG. 1 illustrates one embodiment of a piping stick 100. The piping stick can be made from a variety of components, including, for example, components used in completing a zone-control unit. The piping stick can include a plurality of control sections and a plurality of piping sections, and can define a scalable volume including, for example, an interior lumen, including a sealed interior lumen.

The piping stick 100 depicted in the embodiment of FIG. 1 includes a first control section 102 such as, for example, a first hydronic unit, and a second control section 104 such as, for example, a second hydronic unit. In some embodiments, for example, the control sections 102, 104 can include components configured to allow a user and/or Contractor of the zone-control unit to control, adjust, and/or otherwise affect the operation of the zone-control unit. In one embodiment, for example, and as depicted in FIG. 1, the first control section 102 can be an inlet assembly, and the second control section 104 can be an outlet assembly, which inlet and outlet piping assemblies can be referred to as flow assemblies. In one embodiment, for example, the first control section 102 can comprise plurality of flow assemblies, including, for example, a plurality of inlet piping assemblies, a plurality of outlet piping assemblies, and/or a mixture of inlet and outlet piping assemblies. In one embodiment, for example, the second control section 104 can comprise plurality of flow assemblies, including, for example, a plurality of inlet piping assemblies, a plurality of outlet piping assemblies, and/or a mixture of inlet and outlet piping assemblies. In some embodiments in which one or both of the first and/or second control sections 102, 104 comprise a plurality of flow assemblies, the plurality of flow assemblies can be connected to each other via a plurality of piping sections in the same manner, as the first control section 102 is connected to the second control section 104 via a piping section discussed below.

Figure 4:
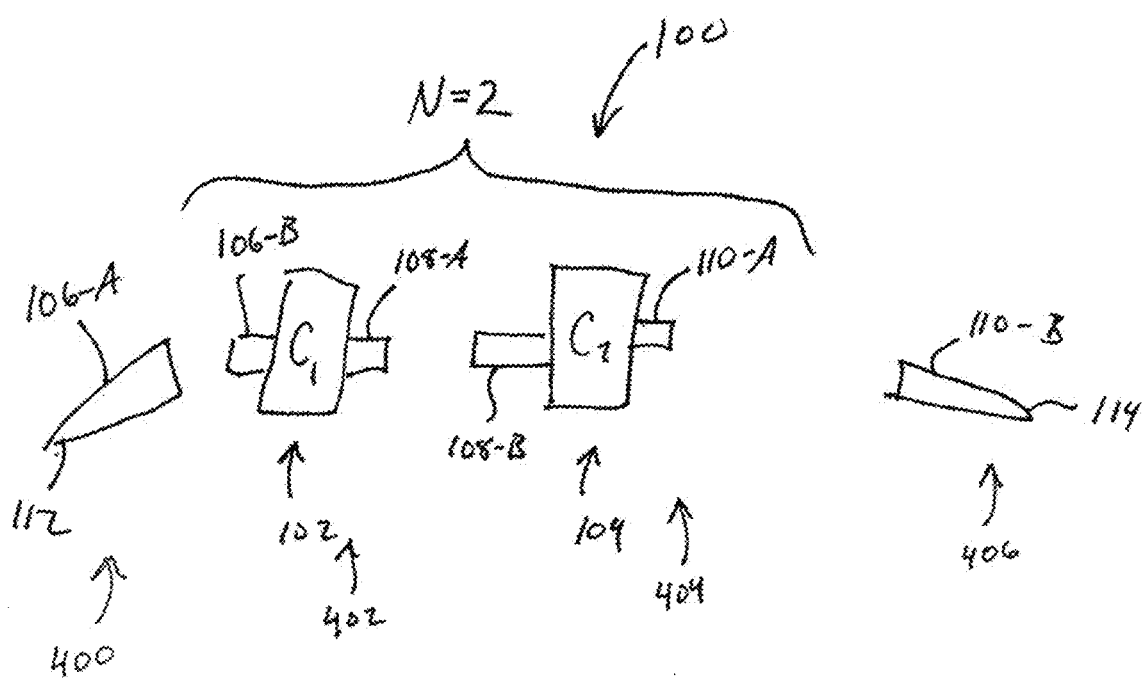
FIG. 4 is a schematic illustration of a plurality of assembly portions created from a single piping stick, according to one embodiment of the present invention.

As further seen in FIG. 4, the number of control sections 102, 104 in the piping stick 100 can be represented by the integer N. In the embodiment depicted in FIG. 4, N=2. In some embodiments, N can be, for example, 1, 3, 3, 4, 5, 6, 7, 8, 9, 10, 20, 50, 100, or any other or intermediate number. In some embodiments, the control sections 102, 104 in a piping stick 100 can include any combination, permutation, or sequence of control sections 102, 104, of inlet and/or outlet piping assemblies, and/or flow assemblies.

The piping stick 100 includes a first piping section 106, a second piping section 108, and a third piping section 110. The piping sections 106, 108, 110 can mechanically and fluidly connect to the control sections 102, 104 and connect the control sections 102, 104. In some embodiments, for example, the piping sections 106, 108, 110 can, in connection with the control sections 102, 104 define and enclose a volume of the piping stick 100.

The piping sections 106, 108, 110 can be made of pipe that can have any desired shape and/or dimensional properties. In some embodiments, for example, the piping sections 106, 108, 110 can be tubular. In some embodiments, for example the piping sections 106, 108, 110 can be made from a variety of materials including, for example, a natural and/or man-made material including, for example, metal such as copper, aluminum, brass, steel, and/or iron, plastic, polymer, composite, or any other desired material. In some embodiments, the shape and/or dimensional properties and material used in the construction of the piping sections 106, 108, 110 can be based on the specific application in which the piping slick 100 will be used.

As seen in FIG. 1, the first piping section 106 includes a first end connecting to the first control section 102 and a second end that is unconnected to another component of the piping stick 100. In some embodiments, for example, the second end of the first piping section 106 can comprise a first cap 112. In some embodiments, for example, the first cap 112 can comprise a spun cap that can, for example, have a thickness that is equal to, less than, and/or greater than the thickness of the wall of the first piping section 106. In one embodiment, for example, the first cap 112 can comprise a thickness that is five times greater than the thickness of the wall of the first piping section 106. The spun cap can comprise the same material and/or a different, material from that used in the other portions of the first piping section 106. In one embodiment in which the first piping section 106 is made of copper, the spun cap can comprise a spun copper cap.

As further seen in FIG. 1, the second piping section 108 includes a first end that is connected to the first control section 102 and a second end that is connected to the second control section 104, and the third piping section 110 includes a first end that is connected to the second control section 104 and a second end that is unconnected to another component of the piping stick 100. In some embodiments, for example, the second end of the third piping stick 110 can comprise a second cap 114. In some embodiments, for example, the second cap 114 can comprise a spun cap that can, for example, have a thickness that is equal to, less than, and/or greater than the thickness of the wall of the second piping section 108, hi one embodiment, for example, the second cap 114 can comprise a thickness that is five times greater than the thickness of the wall of the second piping section 108. The spun cap can comprise the same material and/or a different material from that used in the other portions of the first piping section 106. In one embodiment in which the second piping section 108 is made of copper, the spun cap can comprise a spun copper cap.

As seen in FIG. 1, the first end of the first piping section 106 connects to the first control section 102 via a first union 116. In one embodiment, and as depicted in FIG. 1, a first portion of the first union 116 engages with the first end of the first piping section 106 and the second portion of the first union 116 engages with a portion of a first valve 118. In one embodiment, for example, the first valve 118 can regulate, and direct, and/or control the How of fluid by opening, closing, and/or partially obstructing passageways connected to the first valve 118. The first valve 118 can include a body and a bonnet that together form a casing that hold the fluid that passes through the first valve 118. The first valve 118 can comprise any desired valve type such as, for example, a ball valve, a choke valve, a check valve, a gate valve, a glow valve, or a needle valve.

In one embodiment, the valve 118 can be formed as a portion of a Y-piece 120 including, which can be, a Y-strainer. As seen in FIG. 1, the Y-piece 120 can include a drain 122 located, at one of the ends of the Y-piece 120. In some embodiments, for example, the drain 122 can comprise a drain valve. The drain valve can allow fluid to be drained from the Y-piece 120. In some embodiments, for example, the drain valve can be sealed so as to prevent fluid from draining from and to prevent fluid from entering into the Y-piece 120.

As also seen in FIG. 1, the Y-piece 120 can comprise one or several ports 124. In some embodiments, for example, the ports 124 can be sealed to prevent fluid from draining from and/or from entering into the Y-piece 120. In some embodiments, for example, the one or several ports 124 can be sealed with the corresponding number of plugs. In some embodiments, one or several of these plugs can be removed from one or several of the ports 124 to allow placement of instrumentation so as to access the contents of the Y-piece 120. In some embodiments, for example, this instrumentation can measure the pressure, temperature, or flow rate, of the fluid passing through the Y-piece 120. In one specific embodiment, the ports 124 can include a pressure and temperature (PT) port connected to instrumentation configured to measure the pressure and temperature of the fluid within the Y-piece 120.

The Y-piece 120, and the first control section 102, connect to the second piping section 108 via the second union 126. As seen in FIG. 1, one portion of the second union 126 connects to the Y-piece 120 of the first control unit 102, and the second portion of the second union 126 connects to the second piping section 108.

As further seen in FIG. 1, the second end of the second piping section 108 connects to the second control section 104 via a third union 128. In some embodiments, a portion of the third union 128 connects to the second and of the second piping section 108 and another portion of the third union 128 connects to the second control section 104.

The second control section 104 comprises a variety of components, as seen in FIG. 1, the second control section 104 includes a first pressure and temperature (PT) port 130. Like the PT port discussed above, the first PT port 130 can allow instrumentation to access the fluid contained within and/or passing through the second control section 104 to determine the pressure and/or temperature of that fluid. In some embodiments, for example, the first PT port can be sealed and/or scalable.

As seen in FIG. 1, the second control section 104 can further include, for example, a pressure gauge 132. In some embodiments, the pressure gauge can provide a visual indication of the pressure within the second control section 104 and/or within the piping stick 100. In some embodiments, the pressure gauge 132 can comprise a digital and/or analog pressure gauge, and can provide pressure readings over any desired pressure range and to any desired level of accuracy. In some embodiments, for example, the pressure range and level of accuracy provided by the pressure gauge 132 can correspond to the specific application for which the piping stick 100 is being used.

The second control section 104 can further include a control valve 134 such as, for example, an ATC control valve. In some embodiments, for example, the control valve 134 can comprise a two and or three-way ATC control valve. The ATC control valve may either be of a type that provides only on-off control, or be of type that provides proportional control. An electrical signal can be supplied to the ATC control valve from a controller such as, for example, a DDC controller, via a control signal cable and can energize and control the operation of the ATC control valve. In some embodiments, and as seen in FIG. 1, the control valve 134 can be connected to the second control section 104 via a tailpiece 136.

The second control section 104 can, in some embodiments, include a second pressure and temperature (PT) port 138. The second PT port 138 can allow instrumentation to access the fluid contained within and/or passing through the second control section 104 to determine the pressure and/or temperature of that fluid. In some embodiments, for example, the second PT port can be sealed and or scalable.

The second control section 104 can, in some embodiments, include a second valve 140 which can be, for example, a manual balancing valve. The manual balancing valve can be provided with various features, such as manually adjustable stems tor valve port opening or a combination of a venturi or orifice and an adjustable valve, a stem indicator and/or scale to indicate the relative amount of valve opening, pressure taps to provide readout of the pressure difference across the valve port or the venture/orifice, the capability to be used as a shutoff for future service of the heat transfer terminal, a locking device for field setting the maximum opening of a valve, or a body tapped for attaching drain hose.

Balancing valves, including automatic type (pressure independent) and manual balancing valves are supplied by a water side sales representative and sold directly to the Piping Contractor. There are several manufacturers of balancing valves such as Griswold, Flow design. Nexus, and the like. Isolation valves, drains, air vents and other ancillary piping components are supplied by a water side sales representative and sold directly to the Piping Contractor. There are several manufacturers of these types of products such as Nibco, Gerhard, and the like.

Manual balancing valves can be, for example, field adjusted by water balancing technicians. Automatic/pressure independent balancing valves can maintain the specified GPM regardless of the pressure drop across the coil. Some manual balancing valves are referred to as "circuit setters" which are a type of balancing valve that involves manual balancing. When balancing a system, once a valve is set and the next valve is set, the preceding valve(s) are revisited to adjust the settings again. This is due to the fact that a manual valve involves an adjustable orifice, not a flow controller. Once pressure changes in the system after the initial setting, the flow rate also changes. Such devices typically limit flow when the system is operating at the exact same level as when it was originally set up. In most systems this flow condition typically does not occur because of variable speed pumps and drives. Static, dynamic, and automatic balancing (e.g. Total Authority) valves often require at least 50% less cost in balancing/commissioning as the manual valve. Once set, they may be set forever if no changes have to be made to the flow and system. These types of valves allow for 20 to 30% fewer balancing valves on a project thus reducing static pressure in the system as a whole. Energy consumption over the manual system may be considerable and a consideration in applying these valves. Generally speaking, a 20% savings can be claimed with static and dynamic and potentially larger savings with Total Authority Valves.

As depicted in FIG. 1, the second valve 140 can be attached to and/or integrally formed in Y-piece 142 which can be, for example, a Y-strainer. The Y-piece 142 can connect to the first end of the third piping section 110 via a fourth union 144. A portion of the fourth union 144 can connect to the Y-piece 142 and another portion of the union 144 can connect to the first end of the third piping section 110.

In some embodiments, for example, the piping stick 100 can include one or several flow direction indicators 146. In some embodiments, the flow direction indicators 146 can include a first set of flow direction indicators 146 associated with the first control section 102 and the second set of flow direction indicators 146 associated with the second control section 104. In some embodiments, for example, the flow direction indicators 146 associated with the first and/or second control sections 102, 104 can indicate the direction of fluid flow through the first and/or second control sections 102, 104 when the first and/or second control sections 102, 104 are installed into a zone-control unit. Thus, the flow direction indicators 146 can facilitate the proper attachment of the first and/or second control sections 102, 104 to the zone-control unit.

In some embodiments, for example, the flow direction indicators 146 can be specific to the control section 102, 104 with which they are associated. Thus, for example, in some embodiments the flow direction indicators 146 associated with the first control section 102 can include features distinguishing them from flow direction indicators 146 associated with the second control section 104. These distinguishing features can be any feature capable of allowing differentiation between the first control section 102 and the second control section 104. In some embodiments, these features can include, for example, a human and/or computer readable code, pattern, indicia, and/or text-string.

These distinguishing features can include, for example, an indicator of the function of the control section 102, 104, and/or an indicator of the type of fluid traveling through the control section 102, 104. In some embodiments, for example, the flow direction indicators 146 can include one or several characters indicating the function of the control section 102, 104 and/or the type of fluid traveling through the control section 102, 104 such as, for example, indicating that the first control section 102 is an inlet and/or indicating that the second control section 104 is an outlet and/or indicating that the fluid passing through the first control section 102 is supply thud and/or indicating that the fluid passing. Through the second control section 104 is return fluid.

In one embodiment, for example, the flow direction indicators 146 can include coloration and/or a color scheme to indicate the function of the control section 102, 104 and/or to indicate the type of fluid traveling through the control section 102, 104 with which the flow direction indicators 146 are associated. In one embodiment, for example, the flow direction indicator 146 associated with the first control section 102 can comprise a first color and the flow direction indicator 146 associated with the second control section 104 can comprise a second color. In some embodiments, for example, the first color can be different from the second color. In one embodiment, for example, the flow direction indicators 146 associated with the first control section 102 can include red features such as, for example, one or several red characters, and the flow direction indicators 146 associated with the second control section 104 can include black features such as, for example, one or several black characters.

The flow direction indicators 146 can comprise any feature configured to indicate the desired direction of fluid flow through the first and/or second control sections 102, 104. In one embodiment, for example, the flow direction indicators 146 can be formed into the first and/or second control sections. 102, 104 and/or the first, second, and/or third piping sections 106, 108, 110. In one embodiment, for example, the flow direction indicators 146 can be attached to the first and/or second control sections 102, 104 and/or the first, second, and/or third piping sections 106, 108, 110 and can be, for example, adhered to one or several of those components 102, 104, 106, 108, 110. In one specific embodiment for example, the flow direction indicators 146 can include an indicator of the desired fluid flow direction such as, for example, an arrow, and/or an indicator of a property of the fluid or the type of fluid desire to flow through the first and/or second control sections 102, 104.

In some embodiments, for example, the piping stick 100 can comprise one or several cutting indicators. In some embodiments, cutting indicators can indicate how assembly portions can be created from the piping stick 100. Specifically, in some embodiments, the cutting indicators can indicate where a cut should be made on one of the piping sections 106, 108, 110 to separate the piping stick 100 into assembly portions. In one embodiment, for example, the cutting indicators can be formed into the first and/or second control sections 102, 104 and/or the first, second, and/or third piping sections 106, 108, 110. In one embodiment, for example, the cutting indicators can be attached to the first and/or second control sections 102, 104 and/or the first, second, and/or third piping sections 106, 108, 110 and can be, for example, adhered to one or several of those components 102, 104, 106, 108, 110. In one specific embodiment, for example, the cutting indicators can include an indicator of the desired location for a cut such as, for example, an arrow.

As depicted in FIG. 1, the piping stick 100 includes a plurality of first cutting indicators 148 and a plurality of second cutting indicators 150. As depicted in FIG. 1, the plurality of first, cut indicators 148 indicates a direction in which a cut is desired to be placed, which direction is indicated by a first arrow, and the plurality of second cutting indicators 150 indicates a second direction in which a cut is desired to be placed, which direction is indicated by a second arrow. As further seen in FIG. 1, the first cutting indicators 148 are paired with the second cutting indicators 150 such that the cutting indicators 148, 150 define a region in which each cut can be placed.

The perspective view of FIG. 1A illustrates one embodiment of a piping stick assembly 100-A. In contrast to the piping stick 100 depicted in FIG. 1, the piping stick assembly 100-A comprises a two-piece piping stick assembly 100-A. Specifically, the piping stick assembly 100-A includes a first stick portion of 170 and the second stick portion 172. Both the first stick portion 170 and the second stick portion 172 include one of the control sections 102, 104, and piping sections 174, 176, 178, 180 connected to the one of the control section 102, 104.

The first stick portion 170 of the piping stick assembly 100-A includes a first piping section 174. The first piping section 174 includes a first cap 112 at a first end and is connected to the first control section 102 at a second end. The first stick portion 170 of the piping stick assembly 500-A also includes a second piping section 176. The second piping section 176 includes second cap 114 at a first end and is connected to the first control section 102 at a second end. The piping sections 174, 176 can include the features and properties of the piping sections 106, 108, 110 discussed above.

The second stick portion 172 of the piping stick assembly 100-A includes a third piping section 178. The third piping section 178 includes a first cap 112 at a first end and is connected to the second control section 104 at a second end. The second stick portion 172 of the piping stick assembly 100-A also includes a fourth piping section 180. The fourth piping section 180 includes second cap 114 at a first end and is connected to the second control section 104 at a second end.

The piping sections. 178, 180 can include the features and properties of the piping sections 106, 108, 110 discussed above.

In some embodiments, for example, the first stick portion 170 and the second stick portion 172 can be inserted into and/or stored in handles 252. The details of the handles 252 will be discussed at greater length below with reference to FIGS. 2, 3, and 4A. Further details regarding the handles 252, also referred to as brackets, and alternate embodiments of the handles are found in U.S. Pat. No. 6,951,324, filed Sep. 17, 2003, the entirety of which is hereby incorporated by reference herein.

Figure 3:
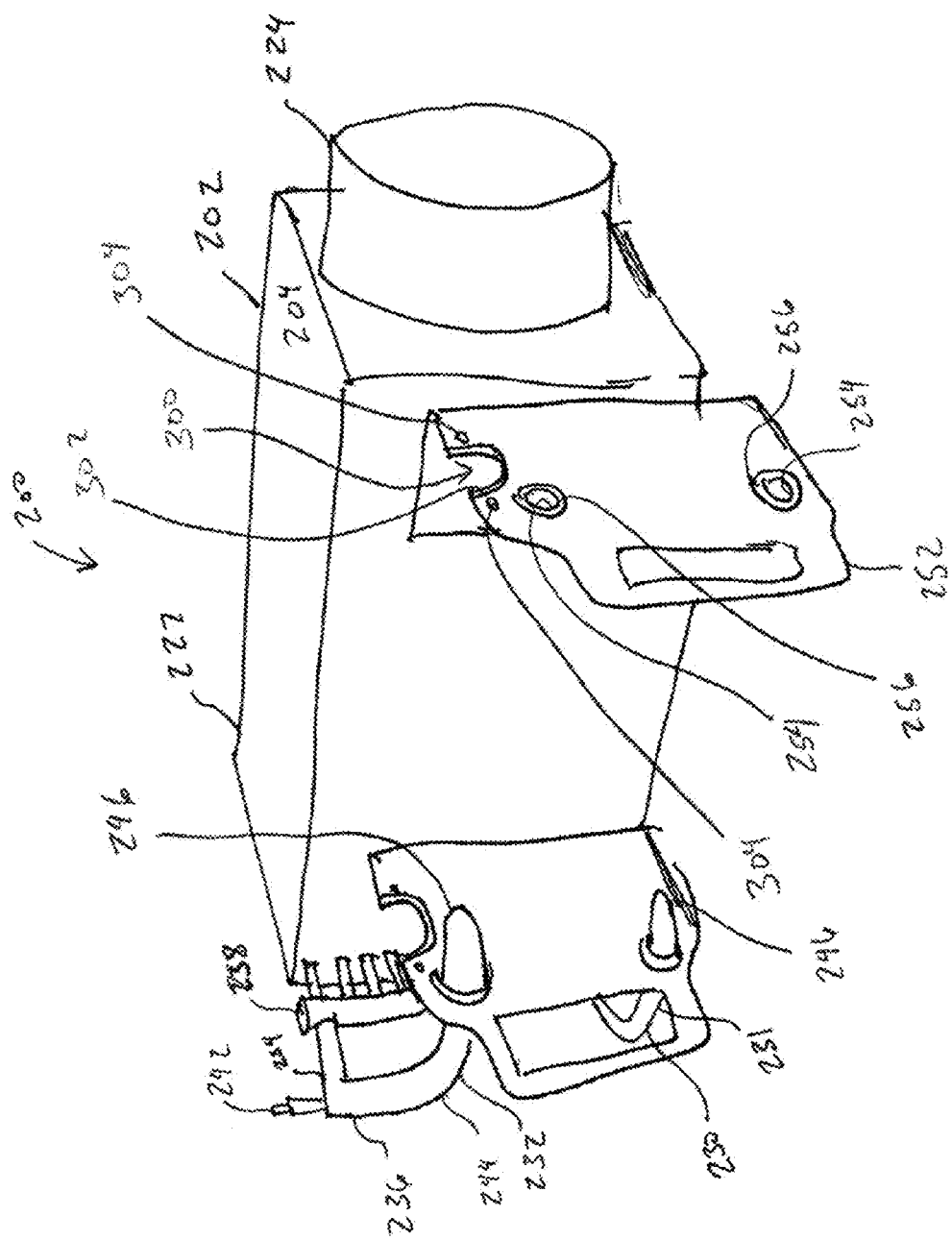
FIG. 3 is a perspective view of a fully-functional zone-control unit ready for installation in a HVAC system, the zone-control unit includes a easing from which a pair of handles project, the handles include a cut out section for supporting the piping stick, according to one embodiment of the present invention.

The piping stick 100 can be provided to the contractor separate from and/or with a zone-control unit. FIGS. 2 and 3 depict embodiments of the zone-control unit adapted for receiving the piping stick 100 so that the piping stick 100 can be provided to the contractor with the zone-control unit.

The perspective view of FIG. 2 illustrates a fully-functional zone-control unit referred to by the general reference character 200, also referred to herein as an HVAC terminal unit. Further details relating to the zone-control unit 200 can be found in U.S. patent application Ser. No. 11/972,479, filed Jan. 10, 2008, and published as U.S. Publication No. 2008/0164006, published on Jul. 10, 2008, the entirety of which is hereby incorporated by reference herein.

The fully-functional zone-control unit 200 depicted in FIG. 2, which illustrates one embodiment of the present invention, preferably includes a mechanical terminal unit 202 having a casing 204. The casing 204, which can be made from various materials of differing thicknesses, is frequently made from galvanized sheet steel material. Frequently, the casing 204 is lined with a thermal insulation material, not visible in FIG. 2, which may be chosen from various different types such as fiberglass insulation, rigid duct board fiber insulation, polyolefin, closed cell, foam insulation, etc. In some embodiments, insulation contained in zone-control unit 200 complies with an industry standard, such as a standard set by the Office of Statewide Health and Planning Department (OSH-POD).

For VAV zone-control units 200, the mechanical terminal unit 202 preferably includes a damper assembly, not visible in FIG. 2. The damper assembly is supported for rotation within the easing 204 by a shaft which extends through and beyond the casing 204. The mechanical terminal unit 202 of a zone-control unit 200 that includes the damper assembly also includes a DDC controller (not shown) that is coupled to a damper motor, (not shown), which rotates the damper assembly. The DDC controller receives a signal from a thermostat or room sensor and responsive thereto controls operation of the damper assembly to regulate the amount of heating or cooling provided by air leaving the zone-control unit 200. The DDC controller may be selected from various different types such as pneumatic, analog electronic or direct digital electronic. The mechanical terminal unit 202 also includes an airflow sensor, also not visible in FIG. 2, which can be located near an air inlet to the easing 204 and may be selected from various types for sensing the velocity of air entering the casing 204.

To heat or cool air flowing through the mechanical terminal unit 202, the casing 204 includes a coil 222 that is located near the air inlet thereto, and which adapts the mechanical terminal unit 202 for inclusion in a hydronic HVAC system. The casing 204 includes both an inlet collar, not visible in FIG. 2, and an outlet connection 224, each of which is adapted to mate with a building's HVAC ductwork. If a zone-control unit 200 were to be assembled at a construction site, the mechanical terminal unit 202 would arrive there with the various components listed above mostly assembled, other than the DDC controller and the damper motor, by the terminal unit's manufacturer.

The mechanical terminal unit 202 is preferably selected from among various different types and styles sold by Krueger based in Richardson, Tex. Krueger is a division of Air Systems Components (ASC) which is part of the Dayton, Ohio Air System Components Division of Tomkins Industries, Inc. of London, England.

To fashion the mechanical terminal unit 202 into a zone-control unit 200 ready for installation into a building's HVAC system, various plumbing components can be added for circulating either hot or cold water through the coil 222. For supplying water to the coil 222 the zone-control unit 100 includes an inlet piping assembly 230. The piping assembly 230 includes an L-shaped section of pipe 231 which connects at one end to a lower header of the coil 222, not visible in FIG. 2.

The zone-control unit 200 also includes an outlet piping assembly 232 for receiving water from the coil 222. A short length of pipe 234 which ends in a tee 236 connects to a header 238 of the coil 222. A manual air vent 242 is connected to and projects upwards above the tee 236 to facilitate eliminating air from the piping assemblies 230, 232 following first assembling the HVAC system, or reassembly of the zone-control unit 100 when maintenance or repairs become necessary. An L-shaped section of pipe 244 is connected to and descends below the tee 236. Also in accordance with embodiments of the present invention, each pipe 231, 244 is sealed by a spun copper cap 246 which can be five (5) times thicker than the pipe 231, 244.

To reduce any possibility that a zone-control unit 200 might be damaged while being transported from its assembly, test and qualification location to a construction site and to facilitate handling the zone-control unit 200 during its installation into the HVAC system, in accordance with the embodiment of the present invention illustrated in FIG. 2 each zone-control unit 200 also includes a pair of handles 252 that are preferably secured to the casing 204 of the mechanical terminal unit 102 near opposite ends thereof.

Each of the handles 252 includes an L-shaped handle mounting bracket 255 which is rigidly secured to the mechanical terminal unit 202 on the side nearest to the piping assemblies 230, 232. As depicted in FIG. 2, the handle mounting brackets 255 are secured near opposite ends of the zone-control unit's casing 204. Each of the handles 252, for example illustrated in FIG. 2, is formed by a plate of sheet metal.

The handles 252 can include features configure to secure the piping assemblies 230, 232 and to secure and/or support the piping stick 100. In the embodiment depicted in FIG. 2, each handle 252 is pierced by a plurality of circularly-shaped holes 254. The holes 254 each receive a grommet 256 that fits snugly around the piping assemblies 230, 232 and/or the piping stick 100 where they pass through the handles 252. In the embodiment, depicted in FIG. 3, the handles 252 can include, a cut-out 300 that is sized and shaped to receive the piping stick 100. The cut-outs 300 can comprise a variety of shapes, including, for example, C-shaped, L-shaped, or any other desired shape. The cut-outs 300 can be lined with the cushioning material 304 that can fit snugly around the piping stick 100 where it contacts the handles 252. In some embodiments, and as depicted in FIG. 3, the handles 252 can include one or more securement features 304. The securement features 304 can be configured to allow the securing of the piping stick 100 to the handles 252. In some embodiments, for example, the securement features can comprise one or several holes located on opposite sides of the cutouts 300 to thereby allow the use of a tie such as, for example, a wire and/or string to secure the piping stick 100 to the handles 252.

Arranged in this way, the handles 252 provide a structure for mechanically coupling the mechanical terminal unit 202 and the piping assemblies 230, 232 together thereby reducing any possibility that the zone-control unit 200 might be damaged while being transported from its assembly, test and qualification location to a construction site. Furthermore, the handles 252 protect zone-control units 200 during shipping, and facilitate their handling during installation into the HVAC system such as maneuvering zone-control units 200 into position in a building's ductwork. During installation, the handles 252 maintain positional relation-ships between the mechanical terminal unit 202 including the coil 222 and the piping assemblies 230, 232 because the handles 252 mechanically bind the entire zone-control unit 200 together into a single unit.

FIG. 4 depicts a schematic illustration of one embodiment of assembly portions created from a piping stick 100. As seen in FIG. 4, the piping stick 100 has been converted to a first assembly portion 400, a second assembly portion 402, third assembly portion 404, and a fourth assembly portion 406. The assembly portions can include portions of the piping stick 100 attachable to the zone-control unit 200, and specifically to the piping assemblies 230, 232 of the zone-control unit 200, and portions the piping stick 100 that are not attachable to the zone-control unit 200.

As seen in FIG. 4, the first assembly portion 400 comprises a first portion 106-A of the first piping section 106 and the first cap 112. In the embodiment depicted in FIG. 4, the first assembly portion 400 is not attachable to the zone-control unit 200.

As seen in FIG. 4, the second assembly portion 402 comprises a second portion 106-B of the first piping section 106, the first control section 102, and a first portion 108-A of the second piping section 108. In the embodiment depicted in FIG. 4, the second assembly portion 402 is attachable to inlet piping assembly 230, and specifically, the second portion 106-B of the first piping section 106 is attachable to a portion of the inlet piping assembly 230 that is exposed by the removal of spun copper cap 246.

As seen in FIG. 4, the third assembly portion 404 comprises a second portion 108-B of the second piping section 108, the second control section 104, and a first portion 110-A of the third piping section 110. In the embodiment depicted in FIG. 4, the third assembly portion 404 is attachable to outlet piping assembly 232, and specifically, the second portion 108-B of the second piping section 108 is attachable to a portion of the outlet piping assembly 232 that is exposed by the removal of spun copper cap 246.

As seen in FIG. 4, the fourth assembly portion 406 comprises a second portion 110-B of the third piping section 110 and the second cap 114. In the embodiment depicted in FIG. 4, the fourth assembly portion 406 is not attachable to the zone-control unit 200.

FIG. 4A is a perspective view of a fully-functional zone-control unit 200 includes a casing 204 from, which a pair of handles 252 project, and the second and third assembly portions 402, 404 that include control sections 102, 104. As depicted in FIG. 4A, the second and third assembly portions 402, 404 are connected to inlet and outlet piping assemblies 230, 232. Specifically, the second assembly portion 402 is connected to pipe 231 of the inlet piping assembly 230, and the third assembly portion 404 is connected to pipe 244 of the outlet piping assembly 232. In some embodiments, for example, the assembly portions 402, 404 can be connected to the inlet and outlet piping assemblies 230, 232 in any desired fashion. In some embodiments, this connection can be made, for example, with a union, by mechanically connecting the pieces together, by welding the pieces together, by soldering the pieces together, by brazing the pieces together, and/or adhering the pieces together.

In some embodiments, for example, the unconnected end of the assembly portions 402, 404, the end that is not connected to the piping assemblies 230, 232 can be connected to other portions of an HVAC system. In some embodiments, for example, this can include connecting the unconnected end of the assembly portions 402, 404 to return and/or supply piping. In some embodiments, the return and/or supply piping can transport fluid to and from the assembly portions 402, 404 and the zone-control unit 200. In some embodiments, for example, the semi-portions 402, 404 can be connected to other portions of the HVAC system in any desired fashion. In some embodiments, this connection can be made, for example, with a union, by mechanically connecting the pieces together, by welding the pieces together, by soldering the pieces together, by brazing the pieces together, and/or adhering the pieces together.

In some embodiments, for example, the assembly portions 402, 404 can interact with the handles 252 via the piping assemblies 230, 232 and/or the other portions of the HVAC system which can be, for example, extend through holes 254 of the handles 252, and specifically extend through the grommet 256 located in the holes 254 of the handle 252. In some embodiments, for example, portions of the assembly portions 402, 404 can extend through the holes 254 of the handles 252, and specifically extend through the grommet 256 located in the holes 254 of the handles 250 to thereby connect the assembly portions 402, 404 with the handles 252. The interaction of the assembly portions 402, 404 with the handles 252 can secure the assembly portions 402, 404 relative to the zone-control unit 200.

Figure 5:
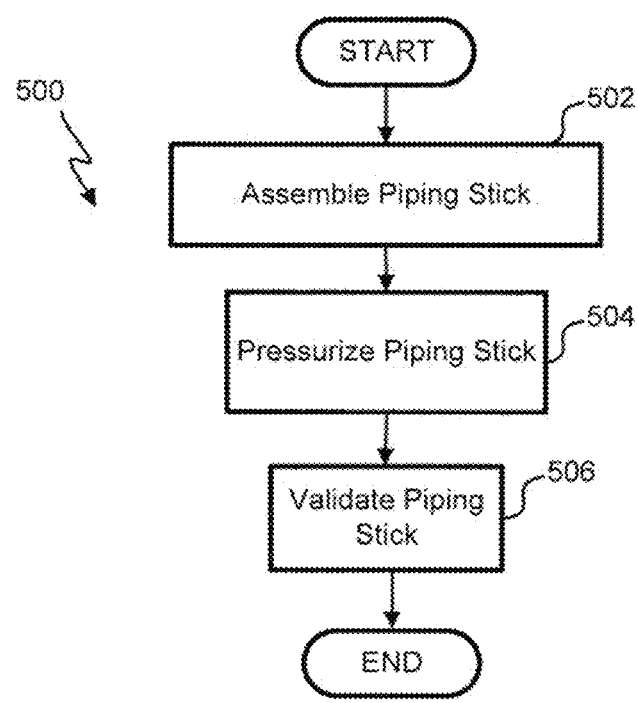
FIG. 5 is a flowchart depicting one embodiment of a process for creating a piping stick.

FIG. 5 is a flowchart illustrating one embodiment of a process 500 for creating a piping stick 100. In some embodiments, the process 500 can be performed at the site of the assembly of the HVAC system and in some embodiments, the process 500 can be performed at a site remote from the assembly of the HVAC system such as, for example, in a factory.

The process 500 begins at block 502 wherein the piping stick 100 is assembled. Assembling the piping stick 100 can include the collection of the components to be used in the piping stick 100 and the connection of the components to be used in the piping stick 100.

After the piping stick 100 has been assembled, the process 500 proceeds to block 504 wherein the piping stick 100 is pressurized. In some embodiments, for example, the piping stick 100 can be pressurized by increasing the pressure within the piping stick 100 and/or by decreasing the pressure within the piping stick 100. Thus, in some embodiments, the pressure within the piping stick 100 is less than and/or greater than ambient pressures. In some embodiments, for example, the pressure within the piping stick 100 can be changed by reusing fluid from the piping stick 100 and or by adding fluid to the piping stick 100.

After the piping stick has been pressurized, the process 500 proceeds to block 506 wherein the piping slick 100 is validated. In some embodiments, for example, validation the piping stick 100 can include determining whether the piping stick 100 is sealed and/or whether the piping stick 100 has leaks. After the piping stick 300 has been validated, the process 500 can terminate.

Figure 6:
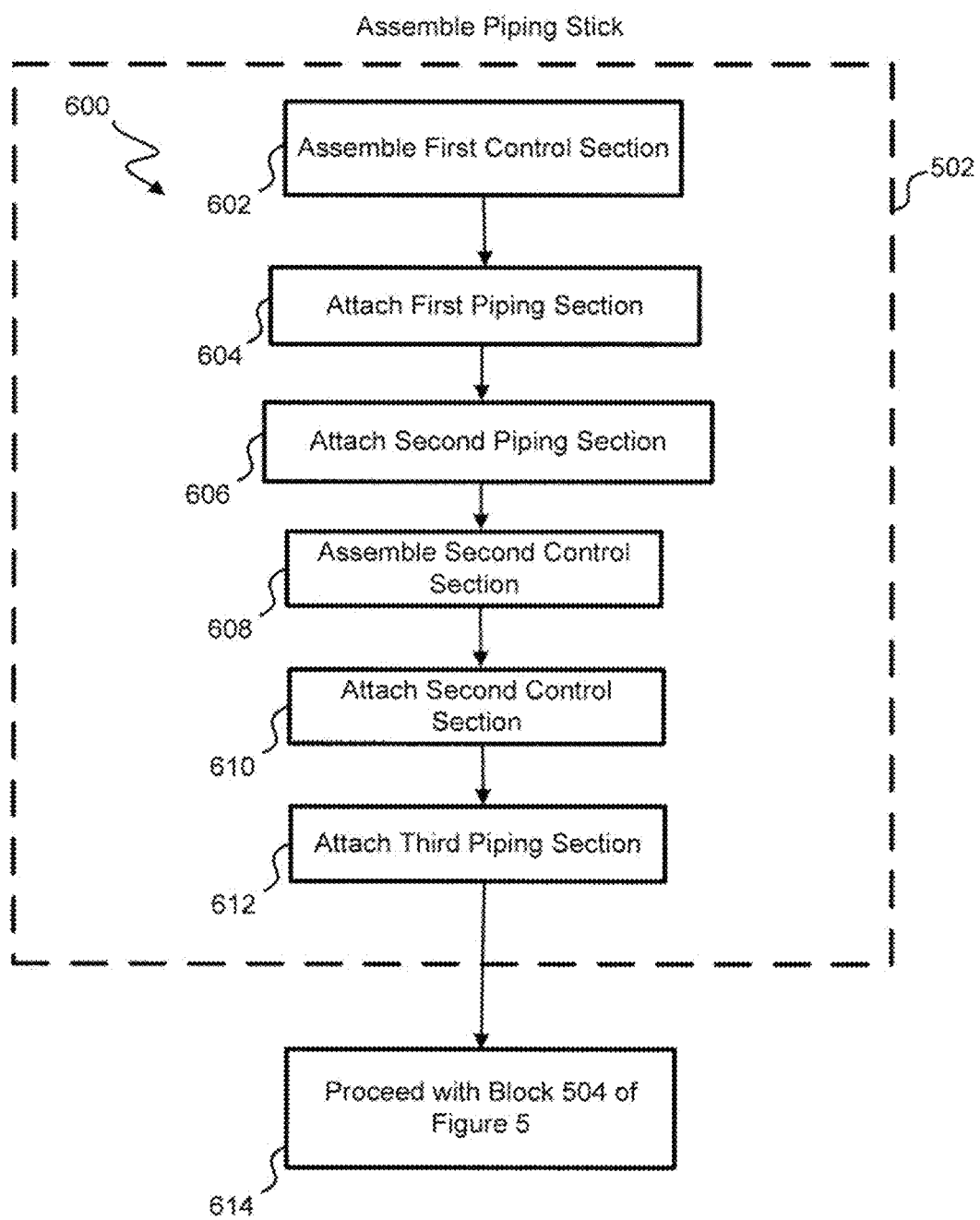
FIG. 6 is a flowchart depicting one embodiment of a process for assembling a piping stick, which process can be performed as part of the process for creating a piping slick depicted in FIG. 5.

FIG. 6 is a flowchart illustrating one embodiment of a process 600 that can be used to assemble the piping stick 100. In some embodiments, for example, the process 600 can be performed as a portion of the assembling of the piping stick 100 described in block 502 of FIG. 5. The process 600 begins at block 602 wherein the first control section 102 is assembled. In some embodiments, for example, the assembly of the first control section 102 can include the collection the components of the first control section 102 and the connection of the components of the first control section 102. In some embodiments, for example, the components of the first control section 102 can be connected to a desired fashion including, for example, screwed and or threaded together, adhere to, brazed, or soldered.

After the first control section 102 is assembled, the process 600 proceeds to block 604 wherein the first piping section 106 is attached. In some embodiments, for example, the first piping section 106 is attached to the first control section 102. As discussed above, in some embodiments, the first piping section 106 can be attached to the first control section 102 via a union.

After the first piping section 106 is attached, the process proceeds to block 606 wherein the second piping section 108 is attached. In some embodiments, for example, the second piping section 108 is attached to the first control section 102. As discussed above, in some embodiments, the first end of the second piping section 108 can be attached to the first control section 102 via a union.

After the second piping section 108 is attached, the process 600 proceeds to block 608 wherein the second control section 104 is assembled. In some embodiments, for example, the assembly of the second control section 104 can include the collection the components of second control section 104 and the connection of the components of the second control section 104. In some embodiments, for example, the components of the second control section 104 can be connected in a desired fashion including, for example, screwed and or threaded together, adhered, brazed, or soldered.

After the second control section 104 is assembled, the process 600 proceeds to block 610 wherein the second control section 104 is attached to the second piping section 108. In some embodiments, for example, the second control section 104 is attached to the second piping section 108. As discussed above, in some embodiments, the second end of the second piping section 108 can be attached to the first control section 102 via a union.

After the second control section 104 is attached, the process 600 proceeds to block 612 wherein the third piping section 310 is attached to the second control section 104. In some embodiments, for example, the third piping section 110 is attached to the second control section 104. As discussed above, in some embodiments, the third piping section 110 can be attached to the second control section 104 via a union. After the third piping section is attached, the process 600 proceeds to block 614 and then proceeds to block 504 of FIG. 5.

Figure 7:
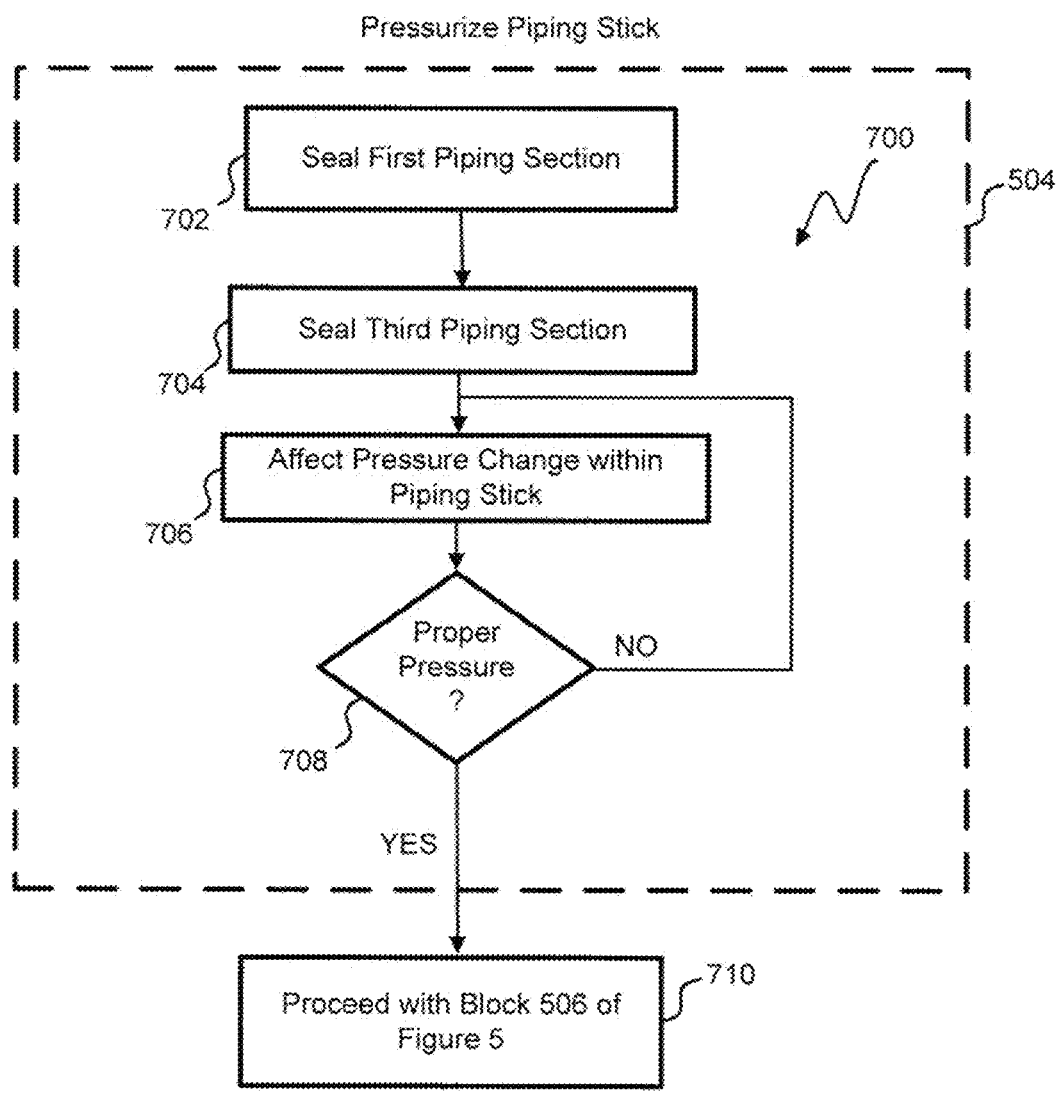
FIG. 7 is a flowchart depicting one embodiment of a process for pressurizing a piping stick, which process can be performed as part of the process for creating a piping stick depicted in FIG. 5.

FIG. 7 is a flowchart illustrating one embodiment of a process 700 that can be used to pressurize the piping stick 100. In some embodiments, for example, the process 700 can be performed as a portion of the pressurizing the piping stick 100 described in block 504 of FIG. 5. The process 700 begins in block 702 wherein the first piping section 106 is sealed. In some embodiments, for example the sealing of the first piping section 106 can include the creation of the first cap 112 to seal the second end of the first piping section 106.

After the first piping section 106 has been sealed, the process 700 proceeds to block 704 wherein the third piping section is sealed. In some embodiments, for example the sealing of the third piping section 110 can include the creation of the second cap 114 to seal the second end of the third piping section 110.

After the third piping section 110 has been sealed, the process 700 proceeds to block 706 wherein a pressure change within the piping stick 100 is affected. In some embodiments, for example, the pressure within the piping stick can be changed by increasing the pressure within the piping stick 100 to a pressure greater than ambient pressure or decreasing the pressure within the piping stick 100 to a pressure less than ambient pressure. In some embodiments, for example the pressure within the piping stick 100 can be increased to a pressure greater than the ambient pressure by adding fluid into the piping stick 100, and in some embodiments, for example, the pressure within the piping stick 100 can be decreased to a pressure less than the ambient pressure by removing fluid from of the piping stick 100. In some embodiments, a pressure change can be affected within the piping stick 100 so that the piping stick 100 attains a desired self-point pressure.

After a pressure change in the piping stick has been affected, the process 700 proceeds to decision state 708 wherein it is determined if the pressure the piping stick 100 is proper. In some embodiments, this determination can include measuring the pressure within the piping stick and comparing the pressure to the desired set-point pressure of the piping stick 100. If it is determined that the pressure the piping stick 100 is improper, the process 700 returns to block 706. If it is determined that the pressure within the piping stick 100 is proper, then the process 700 proceeds to block 710 and to block 506 of FIG. 5.

Figure 8:
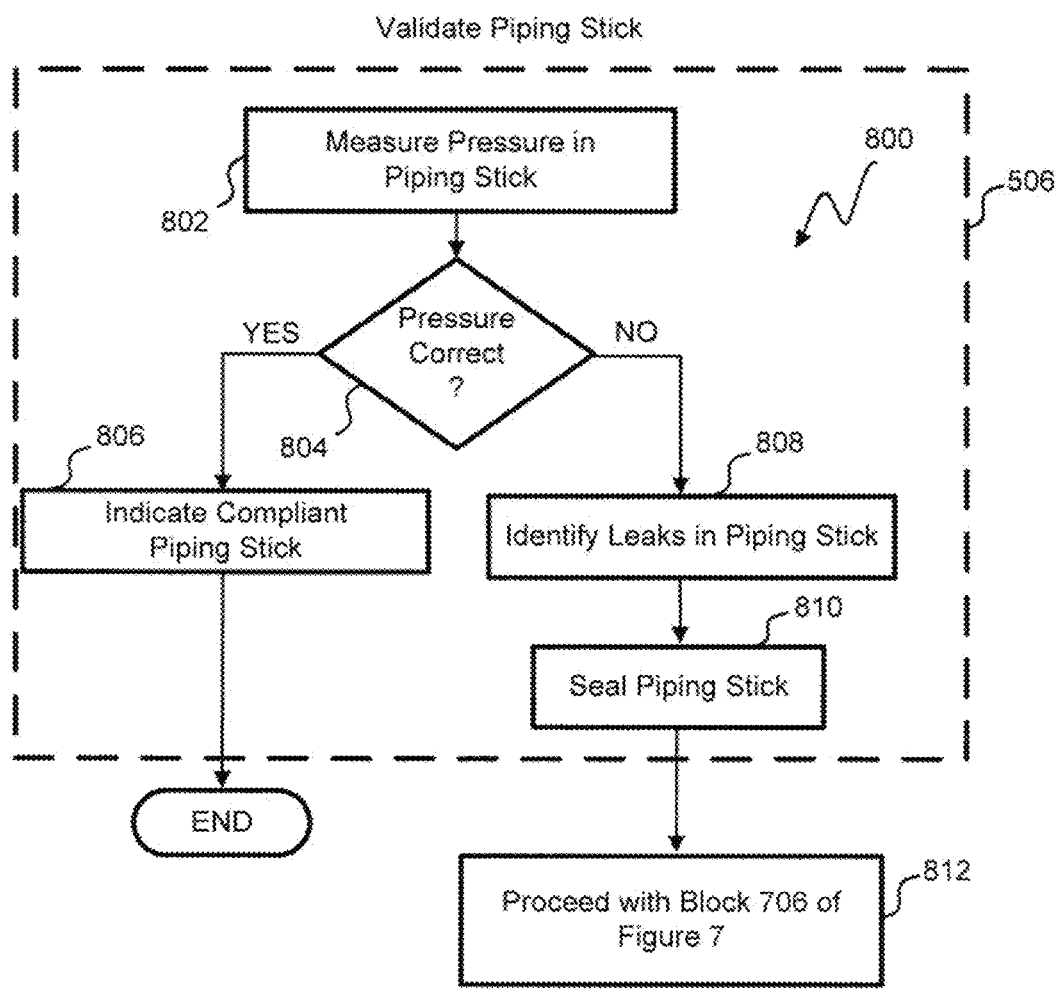
FIG. 8 is a flowchart depicting one embodiment of a process for validating a piping stick, which process can be performed as part of the process for creating a piping stick depicted in FIG. 5.

FIG. 8 is a flowchart illustrating one embodiment of a process 800 for validating a piping stick 100. In some embodiments, for example, the process 800 can be performed as a portion of the validating of the piping stick 100 described in block 506 of FIG. 5. The process 800 begins at block 802 wherein the pressure within the piping stick 100 is measured. In some embodiments, for example, the pressure within the piping stick 100 can be measured by the pressure sensor accessing portion the piping stick 100 through, for example, one of the ports of the piping stick 100.

After the pressure the piping stick 100 has been measured, the process 800 proceeds to decision state 804 wherein it is determined if the measured pressure is correct. In some embodiments, for example, the determination of whether the measured pressure is correct can include comparing the measured pressure within the piping stick 100 to the desired set-point pressure of the piping stick 100.

If it is determined that the measured pressure within the piping stick 100 is correct, the process proceeds to block 806 wherein the piping stick 100 is indicated as compliant, in some embodiments, for example, the indication of the complaint piping stick 100 can comprise an Indication that the piping stick 100 does not have any leaks. Alter the piping stick 100 is indicated as compliant, the process 800 can terminate.

Returning again to decision state 804, if it is determined that the pressure within the piping stick 100 is incorrect, the process 800 proceeds to block 808 wherein leaks within the piping stick 100 are identified. In some embodiments, for example, the identification of the leaks can include testing of each of the joints of the piping stick 100 to identify the location of the leak. In some embodiments, for example identifying the location of any of the leaks can include dividing the pressurized volume of the piping stick 100 into a plurality of smaller pressurized volumes and determining whether the smaller pressurized volumes are losing pressure, which pressure loss provides an indication of a leak within the smaller pressurized volume.

After any leaks in the piping stick 100 have been identified, the process 800 proceeds to block 810 wherein the piping stick 100 is sealed. In some embodiments, for example, the sealing of the piping stick 100 can include the sealing of the leaks identified in block 808. After the identified leaks are sealed, the process 800 proceeds to block 812 and returns to block 706 of FIG. 7.

Figure 9:
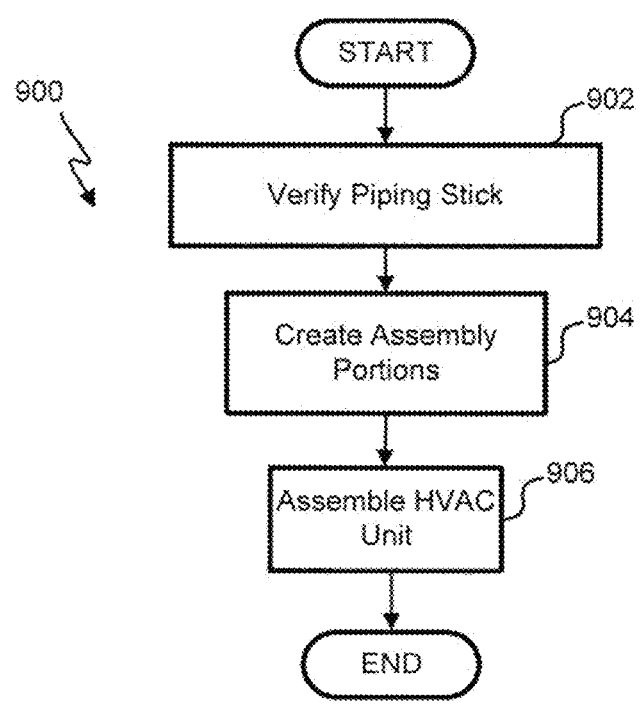
FIG. 9 is a flowchart illustrating one embodiment of a process for assembling an HVAC unit and/or a zone-control unit.

FIG. 9 is a flowchart illustrating one embodiment of a process 900 for assembling an HVAC unit and/or a zone-control unit. The process 900 can be performed by, for example, the contractor. The process begins at block 902 wherein the piping stick is verified. In some embodiments, for example, the verification the piping stick can include ascertaining whether the piping stick is a functional and specified condition. After the piping stick has been verified, the process 900 proceeds to block 904 wherein assembly portions are created. In some embodiments, for example, the assembly portions can be created from the piping stick 100. After the assembly portions are created, the process 900 proceeds to block 906 wherein the HVAC unit is assembled, after which, the process 900 can terminate.

Figure 10:
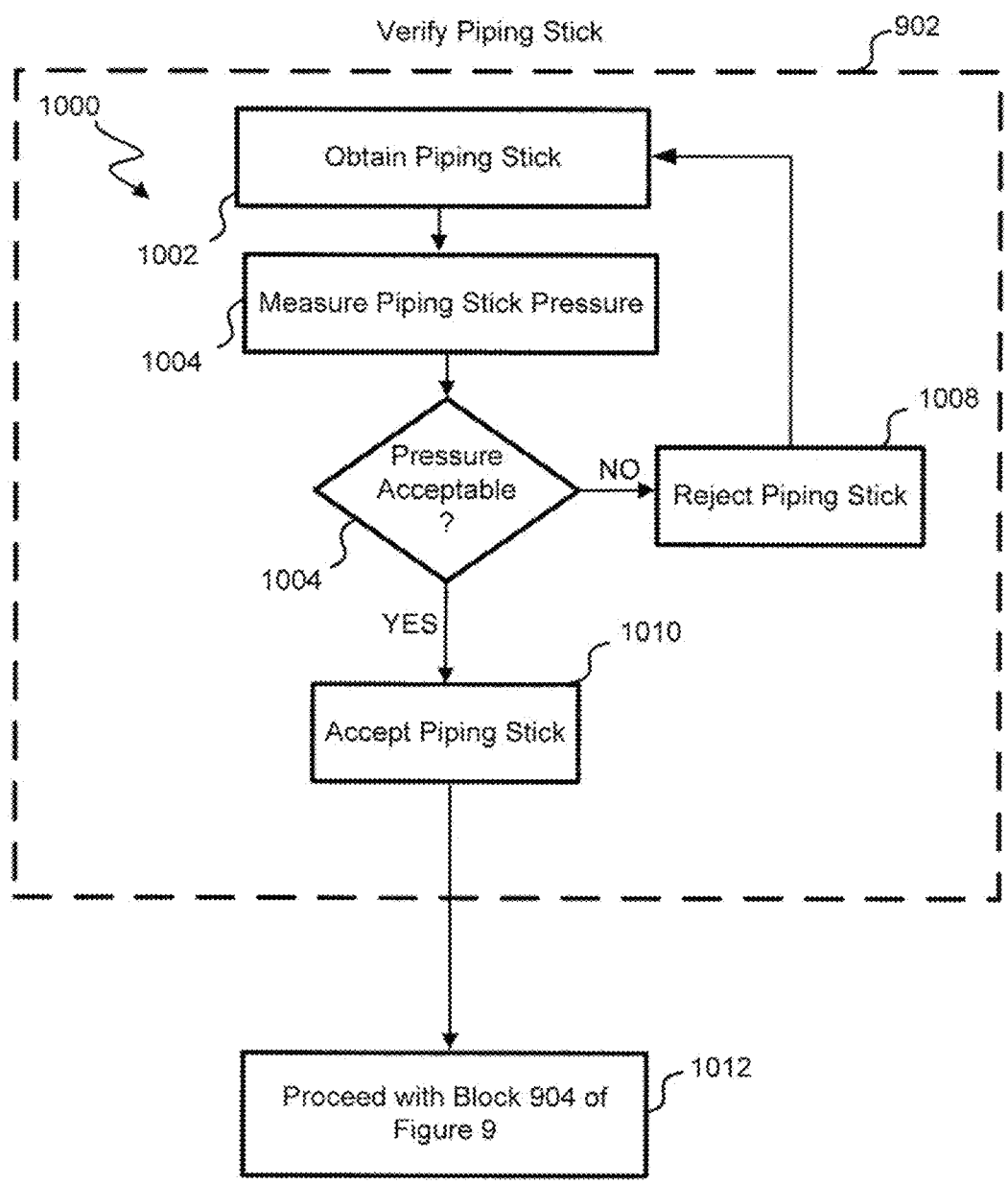
FIG. 10 is a flowchart illustrating one embodiment of a process for verifying a piping stick, which process can be performed as part of the process for assembling an HVAC unit and/or a zone-control unit as depicted in FIG. 9.

FIG. 10 is a flowchart illustrating one embodiment of a process 1000 for verifying the piping stick 100. In some embodiments, for example, the process 1000 can be performed as a portion of the verifying of the piping stick 100 described in block 902 of FIG. 9. The process begins at block 1002, wherein the piping stick 100 is obtained. In some embodiments, for example, the piping stick 100 can be obtained from a supplier of piping sticks 100 such as, for example, a manufacturer, a distributor, a retailer, and/or a service provider. In some embodiments, the piping stick 100 can include information relating to features of the piping stick 100 such as, for example, the set-point pressure of the piping stick 100.

After the piping stick 100 has been obtained, the process 1000 proceeds to block 1004 wherein the piping stick pressure is measured. In some embodiments, for example, the piping stick pressure can be measured by a pressure sensor accessing the interior volume of the piping stick 100 via one of the ports of the piping stick 100. In one embodiment, for example, the pressure of the piping stick 100 can be measured by, for example, the pressure gauge 132.

After the pressure the piping stick has been measured, the process proceeds to decision state 1004 wherein it is determined if the pressure the piping stick is acceptable. In some embodiments, for example, the determination of whether the pressure the piping stick 100 is acceptable can be made by comparing the measured pressure of piping stick 102 to the set-point pressure of the piping stick 100. In some embodiments, for example, the set point pressure the piping stick 100 can include the pressure to which the piping stick 100 was set, as well as the range of acceptable pressures of the piping stick 100.

If the measured pressure of the piping stick 100 is unacceptable, then the process 1000 proceeds to block 1008 wherein the piping stick is rejected. In some embodiments, for example, the rejection of piping stick 100 can include the addition of an indicator of the failure of the piping stick 100 to have a pressure within the acceptable pressure range. After the piping stick. 100 has been rejected, the process 1000 returns to block 1002.

Returning again to decision state 1004, if it is determined that the pressure of the piping stick 100 is acceptable, the process 1000 proceeds to block 1010 wherein the piping stick 100 is accepted. In some embodiments, for example, the acceptance of the piping stick 100 can include the addition of an indicator of the piping stick 100 meeting the acceptable pressure ranges. After the piping stick 100 has been accepted, the process 1000 proceeds to block 1012 and proceeds with block 904 of FIG. 9.

Figure 11:
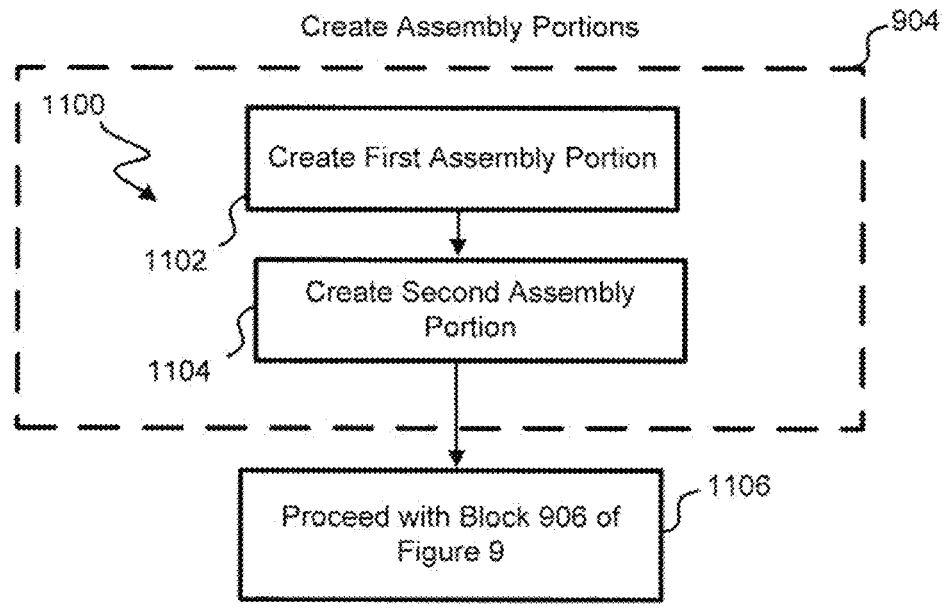
FIG. 11 is a flowchart illustrating one embodiment of a process for creating assembly portions from a piping stick, which process can be performed as part of the process for assembling an HVAC unit and/or a zone-control unit as depicted in FIG. 9.

FIG. 11 is a flowchart illustrating one embodiment, of a process 1100 for creating assembly portions. In some embodiments, for example, the process 1100 can be performed as a portion of creating assembly portions described in block 904 of FIG. 9. The process 1100 begins at block 1102 where in a first assembly portion is created. In some embodiments, for example, the first assembly portion can correspond to one of the assembly portions 400, 402, 404, 406 that is attachable to one of the piping assemblies 230, 232. Specifically, in one embodiment, the first assembly portion can be one of the second assembly portion 402 and/or the third assembly portion 404. The first assembly portion can be created using any desired technique. In some embodiments, for example, the first assembly portion can be created by separating the first assembly portion from the other components of the piping stick 100.

After the first assembly portion has been created, the process 1100 proceeds to block 1104 wherein the second assembly portions created. In some embodiments, for example, the second assembly portion can correspond to one of the assembly portions 400, 402, 404, 406 that is attachable to one of the piping assemblies 230, 232. Specifically, in one embodiment, the second assembly portion can be one of the second assembly portion 402 and/or the third assembly portion 404. The second assembly portion can be created using any desired technique. In some embodiments, for example, the second assembly portion can be created by separating the second assembly portion from the other components of the piping stick 100. After the second assembly portion is created, the process 1100 proceeds to block 1106 and to block 906 of FIG. 9.

Figure 12:
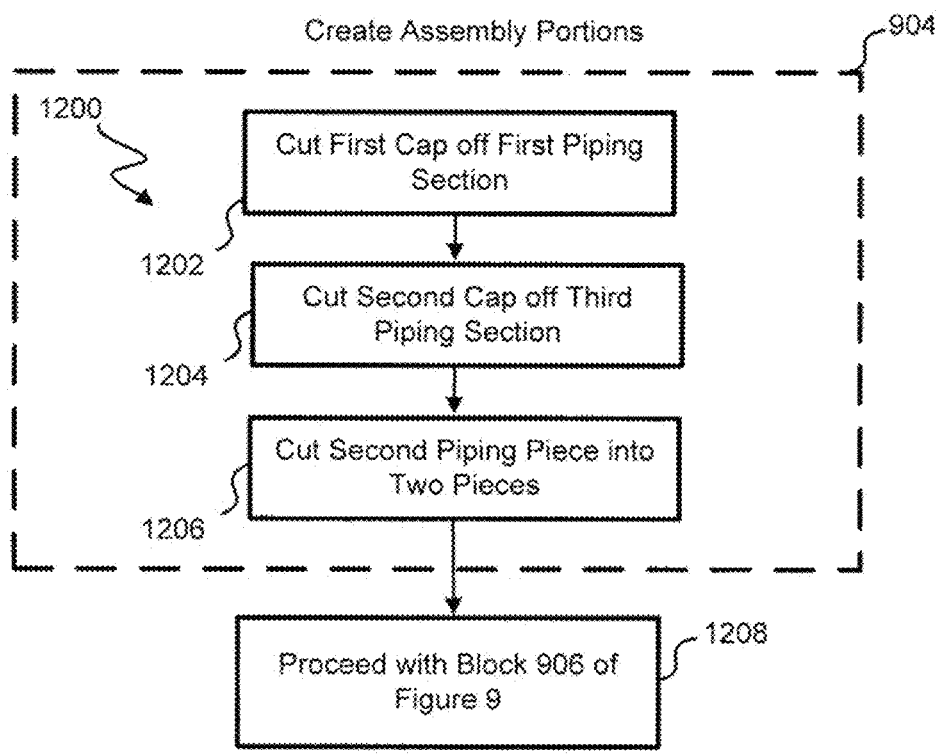
FIG. 12 is a flowchart illustrating one embodiment of a process for creating assembly portions by cutting a piping stick, which process can be performed as part of the process for assembly and HVAC unit and/or zone-control unit as depicted in FIG. 9.

FIG. 12 is a flowchart illustrating another embodiment of a process 1200 for creating assembly portions. In some embodiments, for example, the process 1200 can be performed as a portion of the creating assembly portions described in block 904 of FIG. 9. The process 1200 begins at block 1202 wherein the first cap 112 is cut off of the first piping section 106. In some embodiments, for example, the first cap 112 can be cut off of the first piping section 106 using, for example, a pipe cutter, a saw, tin-snips, a shear, a torch, or any other cutting tool. In some embodiments, for example, the first cap 112 can be cut off of the first piping section 106 by cutting the first piping section 106 between the first end and the second end of the first piping section 106. In some embodiments, for example, the cutting off of the first cap 112 from the other portions of the first piping section 106 can create the first assembly portion 400.

After the first cap 112 has been cut off of the first piping section 106, the process 1200 proceeds to block 1204 wherein the second cap 114 is cut off of the third piping section 110. In some embodiments, for example, the second cap 114 can be cut off of the third piping section 110 using, for example, a pipe cutter, a saw, tin-snips, a shear, a torch, or any other cutting tool. In some embodiments, for example, the second cap 114 can be cut off of the third piping section 110 by cutting the third piping section 110 between the first end and the second end of the third piping section 110. In some embodiments, for example, the cutting off of the second cap 114 from the other portions of the third piping section 110 can create the fourth assembly portion 406.

After the second cap 114 has been cut off of the third piping section 110, the process 1200 proceeds to block 1206 wherein the second piping piece 108 is cut into two pieces. In some embodiments, for example, the second piping section 108 can be cut into two pieces using, for example, a pipe cutter, a saw, tin-snips, a shear, a torch, or any other cutting tool. In some embodiments, for example, the second piping section 108 can be cut into two pieces by cutting the second piping section 108 between its first end and second end. In some embodiments, for example, cutting the second piping section 108 into two pieces can create the second and third assembly portions 402, 404. After the second piping piece 108 is cut into two pieces, the process 1200 proceeds to block 1208 and to block 906 of FIG. 9.

Figure 13:
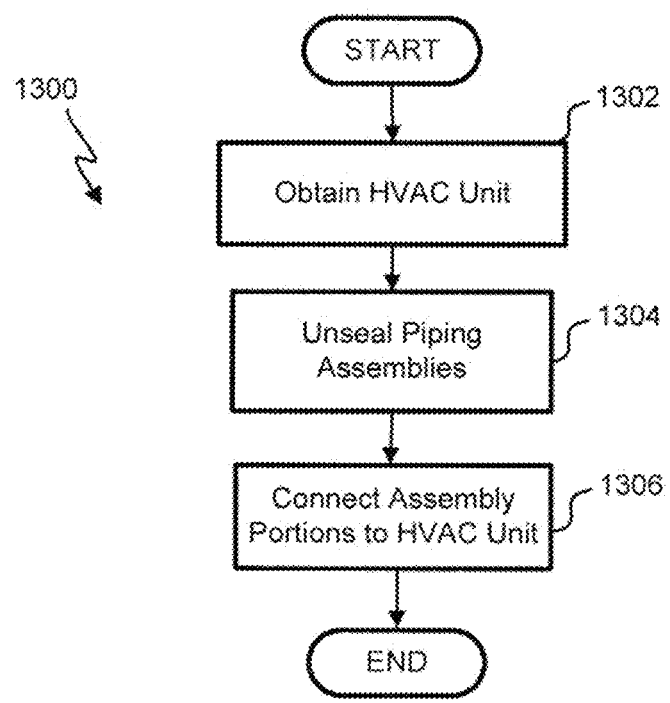
FIG. 13 is a flowchart illustrating one embodiment of a process for preparing an HVAC unit and/or zone-control unit, which process can be performed as part of the process for assembling an HVAC unit and/or zone-control unit as depicted in FIG. 9.

FIG. 13 is a flowchart illustrating one embodiment of a process 1300 for preparing an HVAC unit and/or zone-control unit. In some embodiments, for example, the process 1300 can be performed as part of the process 900 for assembling an HVAC unit and/or zone-control unit as depicted in block 906 of FIG. 9. The process begins at block 1302 wherein an HVAC unit is obtained. In some embodiments, for example, the HVAC unit can include a piping stick 100 as depicted in FIGS. 2 and 3. After the HVAC unit is obtained, the process 1300 proceeds to block 1304 wherein the piping assemblies 230, 232 are unsealed. In some embodiments, for example, the unsealing of the piping assemblies 230, 232 can include, cutting the spun copper caps 246 off of the pipes 231, 244. This cutting can be performed using any that the techniques discussed above in cutting the piping stick 100. After the piping assemblies are unsealed, the process 1300 proceeds to block 1306 wherein the assembly units are connected to the unsealed pipes 231, 244. The connection of the assembly units to the unsealed pipes 231, 244 can be performed using any desired technique including, for example, threading, screwing, adhering, gluing, welding, soldering, or brazing. After the assembly units, are connected with the unsealed pipes 231, 244, the process 1300 can terminate.

Although the present invention has been described in terms of the presently preferred embodiment, it is to be understood that such disclosure is purely illustrative and is not to be interpreted as limiting. Consequently, without departing from the spirit and scope of the invention, various alterations, modifications, and/or alternative applications of the invention will, no doubt, be suggested to those skilled in the art after having read the preceding disclosure. Accordingly, it is intended that the following claims be interpreted as encompassing all alterations, modifications, or alternative applications as fall within the true spirit and scope of the invention.

What is claimed is:

1. A method of manufacturing a piping stick for a coil/thermal transfer device of an HVAC system, comprising:
obtaining a piping stick, the piping stick having a first tubular end section, a second tubular end section, a sealed and pressurized interior lumen defined at least in part by the first and second tubular end sections, a first control section coupled with the first end section, and a second control section coupled with the second end section;
cutting the piping stick to separate the first control section and the second control section; and
incorporating the first and second control sections into the coil/thermal transfer device.

2. The method of claim 1, wherein the first tubular end section comprises a sealed end and a non-sealed end connecting to the first control section.

3. The method of claim 2, further comprising cutting the first tubular end section between the sealed end and the non-sealed end so as to separate the sealed end from the first control section.

4. The method of claim 3, wherein the second tubular end section comprises a sealed end and a non-sealed end connecting to the first control section.

5. The method of claim 4, further comprising cutting the second tubular end section between the sealed end and the non-sealed end so as to separate the sealed end from the second control section.

6. The method of claim 1, wherein the piping stick further comprises an indicator of the location for cutting the piping stick to create the first control section and the second control section.

7. The method of claim 6, wherein cutting the piping stick to create the first control section and the second control section comprises cutting the piping stick at the indicated location.

8. The method of claim 1, wherein the first control section comprises a first valve and the second control section comprises a second valve, wherein the first valve and the second valve are open.

9. The method of claim 1, wherein the first control section comprises a single flow assembly and the second control section comprises a single flow assembly.

10. The method of claim 1, wherein the first control section comprises a plurality of flow assemblies.

11. The method of claim 10, wherein the plurality of flow assemblies are connected by a plurality of piping sections.

12. The method of claim 1, wherein the piping stick comprises a pressure gauge in fluid communication with the interior lumen and indicating a pressure or vacuum.

13. The method of claim 12, further comprising the step of reading the pressure gauge to verify that the sealed interior lumen of the piping stick is either under pressure or vacuum.

14. The method of claim 13, wherein reading the pressure gauge to verify the sealed interior lumen of the piping stick is pressurized to the non-atmospheric pressure further verifies that the first tubular end section and the second tubular end section are pressurized to the non-atmospheric pressure.

* * * * *